(12) United States Patent
Jodaikin et al.

(10) Patent No.: US 8,287,277 B2
(45) Date of Patent: Oct. 16, 2012

(54) RESHAPABLE DEVICE FOR FIXATION AT A DENTAL SITE

(75) Inventors: Ahron Jodaikin, Kiryat Telstone (IL); Hilary Jodaikin, Kiryat Telstone (IL)

(73) Assignee: Colldent V.A. Ltd., Kiryat Yearim (IL)

( * ) Notice: Subject to any disclaimer, the term of this patent is extended or adjusted under 35 U.S.C. 154(b) by 0 days.

(21) Appl. No.: 12/938,692

(22) Filed: Nov. 3, 2010

(65) Prior Publication Data
US 2011/0104635 A1 May 5, 2011

Related U.S. Application Data

(63) Continuation of application No. 11/890,986, filed on Aug. 8, 2007, now Pat. No. 7,850,453.

(51) Int. Cl.
*A61C 17/00* (2006.01)
(52) U.S. Cl. ......................................................... 433/80
(58) Field of Classification Search ............... 433/18, 433/25, 80, 215, 149; 424/435, 469; 132/328, 132/329
See application file for complete search history.

(56) References Cited

U.S. PATENT DOCUMENTS

| | | | |
|---|---|---|---|
| 2,835,628 A | 5/1958 | Saffir | |
| 3,679,360 A | 7/1972 | Bernard et al. | |
| 3,754,332 A | 8/1973 | Warren | |
| 3,923,939 A | 12/1975 | Baker | |
| 5,074,786 A | 12/1981 | Woodward | |
| 4,556,561 A | 12/1985 | Brown et al. | |
| 4,576,190 A | 3/1986 | Youssef et al. | |
| 4,638,823 A | 1/1987 | Newman et al. | |
| 4,685,883 A | 4/1987 | Jernberg | |
| 4,741,700 A | 5/1988 | Barabe | |

(Continued)

FOREIGN PATENT DOCUMENTS
DE 202006003819 6/2006
(Continued)

OTHER PUBLICATIONS

Legler et al., "Definition, Etiology, Epidemiology and Clinical Implications of Dental Carries", Menacker, Harper & Row, pp. 211-225, 1980.

(Continued)

*Primary Examiner* — Cris L Rodriguez
*Assistant Examiner* — Eric Rosen
(74) *Attorney, Agent, or Firm* — Roach Brown McCarthy & Gruber, P.C.; Kevin D. McCarthy

(57) ABSTRACT

A reshapable retention device for insertion at a dental site and contact with adjacent dental surfaces, for the controlled delivery to the dental site of at least one material having a predetermined intraoral activity. The retention device includes at least one matrix containing the material. The retention device is adapted for physically affixing at the dental site for at least a predetermined time period correlated to the delivery of a predetermined portion of the at least one matrix to the dental site in a controlled single, bi or multiphase pattern. The retention device includes a first configuration in which the overall dimensions of the retention device are larger than at least one dimension of the dental site. The first configuration is reshapable to a second configuration in which at least one dimension of the retention device is reduced to enable physically affixing the retention device at the dental site. In the second configuration the retention device includes a predetermined shape having contours for affixing at the dental surfaces.

33 Claims, 7 Drawing Sheets

U.S. PATENT DOCUMENTS

| | | | |
|---|---|---|---|
| 4,772,325 A | 9/1988 | Kwan | |
| 4,837,007 A | 6/1989 | Duckworth et al. | |
| 4,892,483 A | 1/1990 | Douglas | |
| 4,892,736 A | 1/1990 | Goodson | |
| 4,923,683 A | 5/1990 | Sakuma et al. | |
| 4,938,763 A | 7/1990 | Dunn et al. | |
| 5,077,049 A | 12/1991 | Dunn et al. | |
| 5,197,882 A | 3/1993 | Jernberg | |
| 5,278,201 A | 1/1994 | Dunn et al. | |
| 5,324,519 A | 6/1994 | Dunn et al. | |
| 5,373,599 A | 12/1994 | Lemon et al. | |
| 5,460,803 A | 10/1995 | Tung et al. | |
| 5,579,786 A | 12/1996 | Wolk et al. | |
| 5,605,677 A | 2/1997 | Schumann et al. | |
| 5,639,840 A | 6/1997 | Fife et al. | |
| 5,733,950 A | 3/1998 | Dunn et al. | |
| 5,739,176 A | 4/1998 | Dunn et al. | |
| 5,770,182 A | 6/1998 | Fischer | |
| 5,840,329 A | 11/1998 | Bai | |
| 5,869,096 A | 2/1999 | Barclay | |
| 5,875,799 A | 3/1999 | Petrus | |
| 5,998,431 A | 12/1999 | Tseng | |
| 6,068,859 A | 5/2000 | Curatolo | |
| 6,106,811 A | 8/2000 | Gibbs | |
| 6,136,297 A | 10/2000 | Sagel | |
| 6,183,775 B1 | 2/2001 | Ventouras | |
| 6,287,120 B1 | 9/2001 | Wiesel | |
| 6,343,932 B1 | 2/2002 | Wiesel | |
| 6,521,215 B2 | 2/2003 | Okay | |
| 6,565,960 B2 | 5/2003 | Koob et al. | |
| 7,118,376 B2 | 10/2006 | Jodaikin et al. | |
| 2003/0068284 A1* | 4/2003 | Sagel et al. | 424/53 |
| 2005/0175959 A1* | 8/2005 | Jodaikin et al. | 433/80 |

FOREIGN PATENT DOCUMENTS

| | | |
|---|---|---|
| EP | 0389224 | 9/1990 |
| JP | 2001163768 A | 6/2001 |
| WO | 9816503 | 5/1998 |
| WO | 0168038 A2 | 9/2001 |

OTHER PUBLICATIONS

Winston et al. "Caries Prevention in the 21st Century" JADA, vol. 128, pp. 1579-1587, 1998.
Nathanson et al. "In Vitro Elution of Leachable Components form Dental Sealants", JADA, vol. 128, pp. 1517-1523, 1997.
Berry et al. "Amalgram at the New Millennium," JADA, vol. 129, pp. 1547-1556, 1998.
Saxe et al. "Alzheimer's Disease Dental Amalgam and Mercury" JADA, vol. 130, pp. 191-199, 1999.
Soderholm et al., "BIS-GMA-Based Resins in Dentistry: Are they safe?" JADA, vol. 130, pp. 201-209, 1999.
Poole et al., "Remineralization of enamel" Ciba Foundation Symposium, No. 11, Elsevier Scientific Pub. Co., pp. 35-56, 1973.
Donly et al. Evaluating the effects of Fluoride Releasing Central Materials on Adjacent Interporximal Caries: JADA, vol. 130, pp. 817-825, 1999.
Ostrom, "Fluorides in Dentistry" The Environment: Caries Prevention, Menaker L. pp. 445-460, Harper & Row, 1980.
Kautsky et al. "Effect of Salivary Components on Dissolution Rates of Carbonated Apatites" J.B.D. Caries Res. vol. 27, pp. 373-377, 1993.
Guo et al. "Comparison of Fluoride Uptake Produced by Tray and Flossing Methods in vitro" J. Dent, Res. vol. 68, pp. 496-498, 1989.
Rose et al. J. Dent. Res., IADR Abs, vol. 77, pp. 972, 1998.
Rawls, "Preventive Dental Materials: Sustained Delivery of Fluoride and Other Therapeutic Agents", Adv. Dent. Res., vol. 5, pp. 50-55, 1991.
Mandel, "Changing patterns of dental caries" Quinlessence Int., Vo. 16, pp. 81-87, 1985.
Massler, "Preventive Endodontics: Vital Pulp Therapy" Dental Clincis of North America, pp. 663-673, 1967.
Hoffman, "Histopathology of Caries Lesions" The Biological Basis of Dental Caries, Menaker. pp. 226-246, Harper & Row, 1980.
Magazine of Dental Association, "Research on Teeth Separation Rubber with Fluorine Sustained-Release Property" Feb. 10, 2000, Vo. 52, No. 11, Item 74 shown on p. 134.
Addadi, L. and Weiner, s. Angen. Chem. Int. Ed. Engl. 31: 153-169 (1992).
Jodaikin, A. and Goldstein, S. J. Dent 16-140-144, (1988).
Paine, M.L. et al JADA 129, 69-77, (1998).
Zhang, Y.P. et al J. Clin. Dent 14: 23-28, (2003).
Glickman I., Clinical Periodoutology, fourth edition, Saunders p. 18-19 (1972).
Kay L.W. Drugs in Dentistry, Bristol p. 242-243, 254-255 (1972).
Miller, M and Truthe, T. Jada 124:32 (1993).
Bailey, A.J. et al., Biochem. Biophys. Res. Commun. 35:663-671 (1969).
Orban J.M. et al. J of Biomedical Materials Research 68A:756-762, (2004).
Bourges et al Adv. In Colloid and Interface Sci 215-228: 2002.
Bourges X. et al. Biopolymers 63:232-238: 2002.
Jodaikin, A. and Goldstein, S., J. Dent. 16:140-144, (1988).
Harris, N.O. and Christen, A.G. Primary Preventive Dentistry 4th Ed Norwalk Appleton Longe 1995.
Wu. H. et al ,abstract from Hua Zi Kou Qiang Yi Xue Za Zhi 18: 219-221, (2000).
Zimmerman, B.F. et al J. Dent. Res. 63:689-692 (1984).
Hormann, H. In Sigel, H. Metal Ions in Biological Systems vol. 3 New York Marcel and Dekker p. 105, 1974.
Mjor, I.A. Quintessence Int.29: 600-602, 1998.
Remington's Pharmaceutical Sciences, Gennaro A. R. ed., Mack Publishing Company, Easton, Pennsylvania, 1990.
Inaba D. et al., Caries Res. 30:218-224 (1996).
Jenkins, G.N. The Physiology and Biochemistry of the Mouth p. 495, 1978, Blackwell Scientific Publishing.
Craig, R.G. et al Dental Materials, Properties and Manipulation p. 2-28, 2nd Ed 1979 CV Mosby Co.
Koulourides, T., Art and Science of Dental Caries Research pp. 355-378, 1968.
Poole, D.F,G. And Silverstone, L.M., Hard tissue Growth Repair and Remineralisation, pp. 35-52, Ciba Fondation Symposium No. 11, Elsevier Scientific Publishing Company, 1973.
Pearce E.I.F and Moore, A.J., J. Dent Res 64;416-421, 1985.
A guide to the use of fluorides JADA 113:504-564, 1986, prepared by the National Fluoride Task force of the NFDH.
Levi-Kalisman, Y. et al J. Chem Soc. Dalton Trans 2000: 3977-3982, 2000.
Wefel, J.S. and Harless, J.D. J. Dent Res 66: 1640-1643, 1987.
Takagi, S. et al Caries Res 34: 281-288 (2000).
Addadi, L. And Weiner, S. Angew, Chem. Int. Ed. Engl. 31:153-169, (1992).
Kodaka, T. et al Caries Res 26 : 69-76 (1992).
Addadi, L. et al ACS Sym. Series No. 444, 1991.
Turezyn, R. et al J. Biomater Sci. Polym Ed 11:217, (2000).
Wefel J.S. et al. Am J. Dent. 8, 217-220 (1995).
Caufield, P.W. And Navia, J.M. in the Biological Basis of dental caries, Menaker, L. 406-407, Harper and Row, (1980).
Clarkson B.H. et al. J. Dent. Res. 60:1912-1920 (1981).
Shellis, R.P. et al Eur. J. Oral Sci 110: 392-395, (2002).
Clarkson, B.H. et al Caries Res 32: 357, 1998.
Tanaka, K. and Iijima, Y. J. of Dent. 29: 421-426 (2001).
Dental Therapeutics Digest Odontos Pub Inc.: Kay L.W. Drugs in Dentistry, Bristol 1972.
O'Brien, W.J. And Ryge, G. An Outline of Dental Materials, Saunders 1978.
Steinberg, D et al., J. Dent. Res. 67-208 Abstract No. 767, 1988.
Kopel, H.M. et al., J. of Dent. for Child 47: 425-430, (1980)) and Periochip.
Vandelli, M.A. et al J. of Controlled Release 96,67-84 (2004).
Traub W., and Piez, K., A. Adv. Protein Chem. 25:243-352, 1971.
Davis, B.A. et al Caries Res 35, 331-337, (2001).
Takatsuka, T. J. Dent Res. Sp Iss. A #2815 (2002).
Loty C et al J. Biomed. Mat. Res. 49, 423 abstract (2000).
Cury, J.A. et al Caries Res. 37, p. 194-199 (2003).
Exterkate, R.A.M. et al J. Dent Res. 72 1599-1603 (1993).
Zhang et al J. Clin. Dent 14: 23-28 (2003).
Addadi, L. et al ACS Sym. Series No. 444, p. 13-27 (1991).
Addadi et al in Chemistry and Biology of Mineralized Tissues, Ed. Slavkin, H. and Price, P. Elsevier Sci. Pub. BV 153-162 (1992).

* cited by examiner

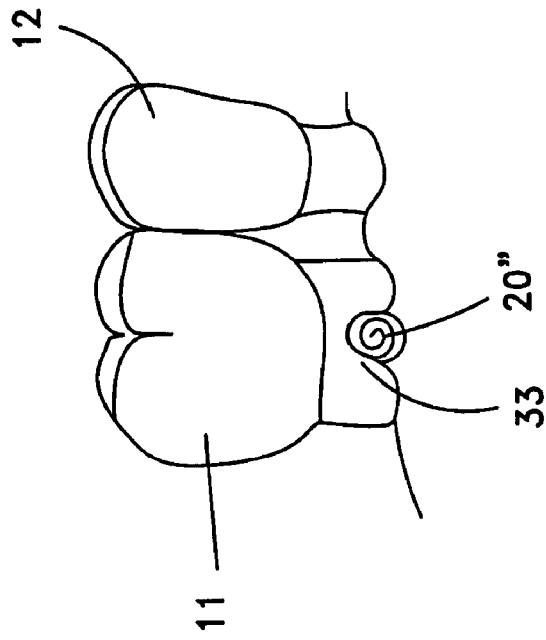
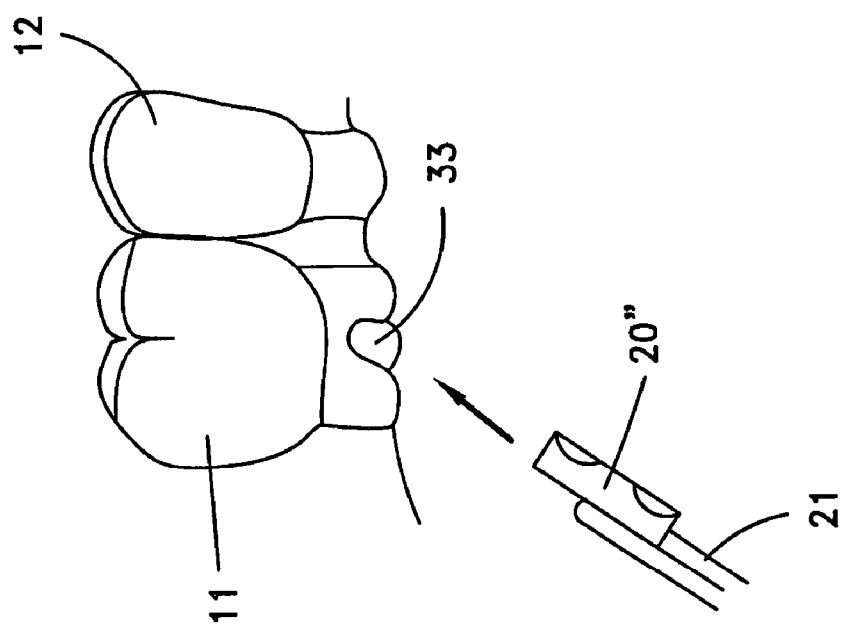

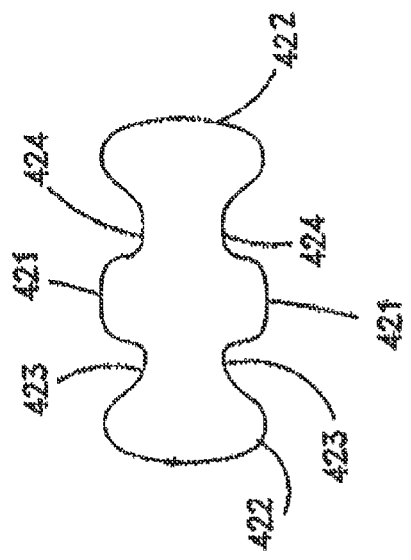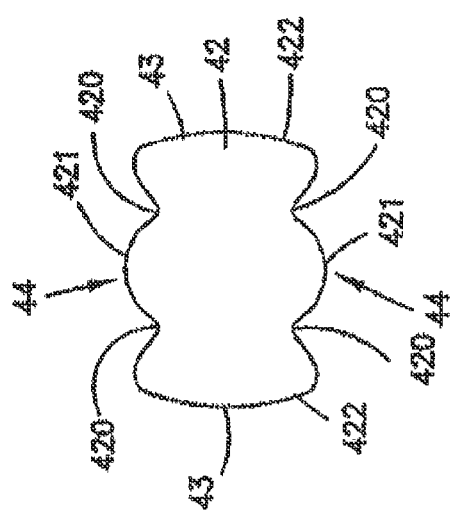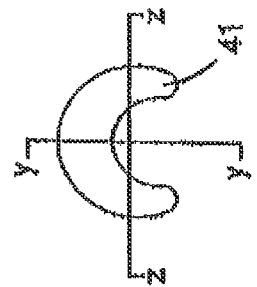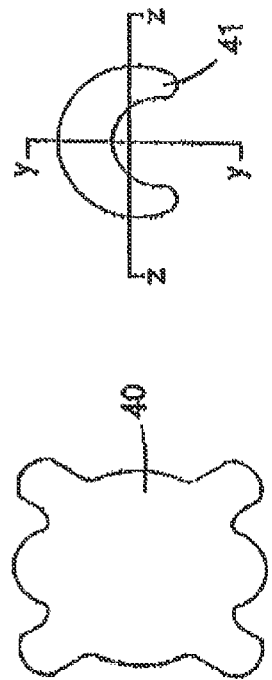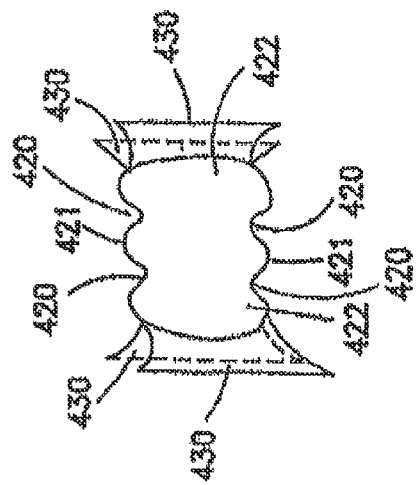

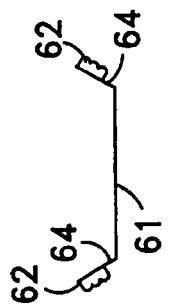
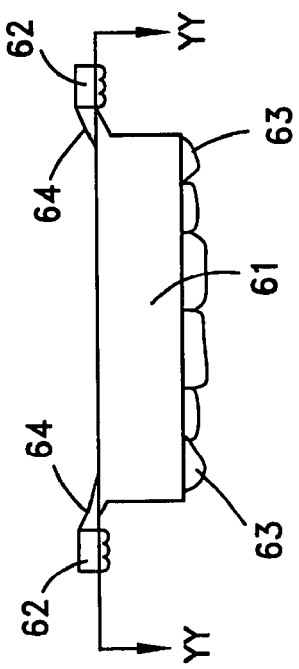
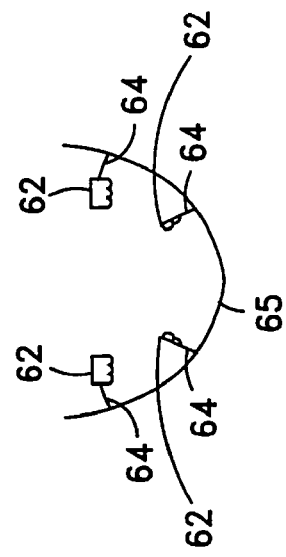

RESHAPABLE DEVICE FOR FIXATION AT A DENTAL SITE

REFERENCE TO CO-PENDING APPLICATIONS

This application claims priority as a continuation of U.S. patent application Ser. No. 11/890,986, filed on Aug. 8, 2007 (now allowed).

FIELD OF THE INVENTION

The present invention relates generally to oral devices. In particular, the present invention relates to oral devices for retention at dental sites within the intraoral cavity to enable, inter alia, any one of the prevention, treatment, diagnosis, elimination, and retardation of oral and other diseases or problems. More particularly, the present invention relates to the chemical treatment of dental surfaces, or for chemical and/or physical restoration of teeth. Even more particularly the present invention is directed at the delivery of fluoridizing and other agents to or from interproximal sites among others.

BACKGROUND OF THE INVENTION

A significant percentage of dental caries (demineralization, decay) occurs between teeth (interproximally, aproximally). This difficult, inaccessible region has been recognized as a problem for more than half a century. Approaches have ranged from grinding of the interproximal surfaces to make them self-cleansing and thus caries "immune" (Mjor, I. A. Quintessence Int. 29: 600-602, 1998) to flossing between the teeth which requires fastidious patient compliance and smooth surfaces. The inclusion of fluoride (U.S. Pat. No. 4,638,823) and other agents in dental floss (U.S. Pat. No. 5,875,799) and other electric (U.S. Pat. No. 5,579,786) or mechanical and chemical devices (U.S. Pat. Nos. 4,576,190, 4,638,823 and 5,373,599) does not appear to have significantly reduced interproximal caries. There is thus, a need to develop a technique or device which overcomes these limitations and the disadvantages of flossing between the teeth.

Various means of chemically preventing or treating such lesions, as well as other problems such as discoloration and sensitivity are described by the inventors of the present invention in U.S. Pat. No. 7,118,376 and its co-pending US Continuation In Part Application, Publication No. 2005-0175959, the contents of which, including publications referenced therein, is fully incorporated herein by reference.

In U.S. Pat. No. 7,118,376 the inventors of the present invention, describe a system for the controlled delivery of at least one material having a predetermined intraoral activity to an interproximal site of at least one dental surface in an oral cavity. The system comprises a polymeric matrix containing the said material. The system is sufficiently flexible for insertion at the interproximal site to be physically affixed thereat and sufficiently tough to maintain mechanical integrity at the interproximal site for the required amount of time and for a predetermined amount of time. The interproximal site is defined in U.S. Pat. No. 7,118,376 as an area of contact and surrounding surfaces between the dental surface and an adjacent dental surface. The co-pending US Continuation In Part Application, Publication No. 2005-0175959, discloses the delivery of a predetermined portion of the at least one matrix to the interproximal site in a controlled single, bi or multiphase pattern.

However, the system described in U.S. Pat. No. 7,118,376 and its co-pending US Continuation In Part Application, Publication No. 2005-0175959 is not directed to gingival and periodontal disease, or to the general systemic treatment or prevention related to the oral cavity and digestive system. Moreover, they do not relate to subtle anatomic nuances of the dentition and gingival and periodontal tissue in healthy or pathologic states.

The restoration of interproximal cavities, for example dental filling procedures, requires packed filling material to be retained in position in a tooth for a period of time. A thin flexible strip made of metal, plastic or other suitable material, known as a dental matrix band (or band, or matrix) is typically wrapped around the sides of the tooth being restored to maintain the filling in place while and after the filing has been placed to prevent the filling from distorting or flowing out of the desired tooth contour. Thus, a matrix band acts as a template to facilitate reestablishment of lost tooth contour by the filling material. A small wedge is often used, lodged in the interproximal space between the band and adjacent tooth to urge the band into close contact with the tooth being restored, and thus ensure that the band is held properly in place. A retention device that is fine tuned to anatomical nuances of the interproximal site and that limits and avoids the need for a wedge will facilitate proper placement of the matrix band at the interproximal site without encroaching on and/or causing damage to the gingiva or at least limiting such damage. Moreover, a retention device that itself acts as a template to facilitate reestablishment of lost tooth contour by the filling material may minimize costs involved with such procedures by reducing the amount of time and maximizing efficiency of the procedure.

It is therefore an object of the present invention to provide a retention device for physically affixing at a dental site.

An additional object of the present invention is to provide a reshapable device for physically affixing at a dental site to have a desired or predetermined activity to at least one desired dental surface in the oral cavity, or into the oral cavity, which overcomes the disadvantages of the prior art.

It is another object of the present invention to provide such a device that is particularly directed to the anatomical areas of interproximal sites and furcations.

It is yet another object of the present invention to provide a system for fixing a plurality of devices intraorally.

It is a further object of the present invention to provide such a device that is configured according to the contours of dental and soft tissue surfaces.

It is still another object of the present invention to provide such a device that employs at least one matrix as a carrier for active material.

It is an additional object of the present invention to provide such a device in which the matrix for the active material may be biodegradable, resorbable or non-resorbable.

It is another object of the present invention to provide such a device which is particularly adapted for physical fixation at a dental site, for at least a predetermined time period, typically sufficient to enable the controlled or sustained delivery of a required quantity of the active material from the matrix or matrices to the surfaces and/or oral cavity.

It is another object of the present invention to provide such a device in which the physical affixing of the device is by way of a physical property of the matrix, in particular wherein the matrix comprises a hydrophilic polymer which softens and swells in situ by the hydration thereof in the oral cavity after accommodation at the dental site.

It is another object of the present invention to provide such a device which is adapted on the one hand to accommodate the matrix and align the same with the dental site, and on the other hand is also adapted for affixing at the site by virtue of its shape, configuration and elasticity/resilience of the material from which it is made. In particular, such adaptation includes sufficient elasticity and toughness of the matrix material, which are important criteria when positioning the matrix between teeth.

It is another object to provide such a system wherein the device is sufficiently flexible for insertion into an interproximal site, and at the same time of sufficient toughness to maintain mechanical integrity thereat, while being soft enough not to be a source of discomfort within the oral cavity prior to its removal or biodegration.

It is another object of the present invention to provide any one or combination of a plurality of chemical and other agents that have a desired activity at the dental site, in particular such as to enable inter alia the cleaning, prevention, treatment, diagnosis, cosmetic treatment (whitening/bleaching and mouth/breath freshening), elimination or retardation of dental caries at tooth surfaces or at tooth interfaces with restorations or prostheses or to treat gingival or periodontal disease.

It is another object of the present invention to provide a system that is shaped to fit over a portion of, or an entire single dental arch.

It is another object of the present invention to provided such a device that is designed to release a chemical agent into the saliva for a desired or predetermined activity therewithin or in the digestive tract or absorption into the body.

It is another object of the present invention to provide such a device which includes at least one adhering agent.

It is another object of the present invention to provide such a device in a specific, controlled micro-environment which selectively excludes at least one element or molecule present in the mouth by way of a physical or chemical property of the matrix or matrices.

It is another object of the present invention to provide such a device in a specific, controlled micro-environment which optimizes the delivery of a least one element, molecule or agent to the said dental site. The said element, molecule or agent can be exogenous, from the device, or endogenous, e.g. directly or indirectly from the saliva.

It is another object of the present invention to provide such a system that employs at least one matrix to deliver a single phase controlled release pattern or a bi- or multiphase controlled release pattern to deliver at least one agent at an appropriate or optimal time, stage, manner or form.

It is another object of the present invention to provide such a system that employs at least one bi- or multi-layer or bi- or multi-located matrix to provide a single phase, biphase or multiphase controlled release system.

It is another object of the present invention to provide such a system that employs at least one matrix which keeps the active material or materials inactive by chemical means such as inhibition or physical separation in order to allow at least one agent to be delivered at an appropriate or optimal time, stage, manner or form.

It is another object of the present invention that the device is adapted to facilitate affixing at least one matrix band at the interproximal site to restore at least one cavity.

It is another object of the present invention that the device itself is adapted physically or chemically to allow the restoration of at least one interproximal cavity.

Additional objects and advantages of the present invention will become apparent as the description proceeds.

SUMMARY OF THE INVENTION

Thus, the present invention provides a method for the prevention and/or treatment of dental caries in a patient in need thereof, comprising applying at a dental site of said patient the matrix or matrices according to the invention, wherein the material is a fluoridation agent. Said material is selected from the group consisting of sodium fluoride, stannous fluoride, acidulated phosphate fluoride, calcium fluoride, an amine fluoride, fluoroaluminosilicate glass and any mixture thereof.

Alternatively, the material of the present invention is an amorphous mineral. Said material is selected from the group consisting of amorphous calcium phosphate, amorphous calcium phosphate fluoride, amorphous calcium carbonate phosphate, amorphous calcium carbonate phosphate fluoride, amorphous calcium fluoride and dicalcium phosphate dehydrate.

Alternatively, the material of the present invention is a crystalline mineral. Said material is selected from the group consisting of aragonite, brushite, calcite, dahltite, ferrhydrite, fluoroapatite, hydroxyapatite, lepidocrocite, magnetite, octocalsium phosphate, vaterite and whitlockite.

Alternatively, the material of the present invention is made of an organic material. Said material is selected from the group consisting of macromolecules such as acidic proteins, glycoproteins or sulfated polysaccharides, or smaller molecules such as polyaspartic or polyglutamic acid.

Alternatively, the material of the present invention is an enhancing agent or further active agent. Said material is selected from the group consisting of calcium chloride, calcium bromide, calcium nitrate, calcium acetate, calcium gluconate, calcium benzoate, calcium glycerophosphate, calcium formate, calcium fumarate, calcium lactate, calcium butyrate, calcium isobutyrate, calcium malate, calcium maleate, calcium propionate, calcium vaerate, alkali salts, ammonium salts of orthophosphoric acid such as potassium sodium or ammonium orthophosphate, monopotassium phosphate, dipotassium phosphate tripotassium phosphate, monosodium phosphate, disodium phosphate and trisodium phosphate.

Alternatively, the material of the present invention is an acidifying, buffering or pH regulating agent. Said material is selected from the group consisting of acidulated phosphate fluoride, citric acid, sodium citrate, sodium bicarbonate, calcium carbonate, arginine and polyacrylic acid fully neutralized with alkalimetal ammonium or (alkylol) amine compound sodium polyacrylate.

Alternatively, the material of the present invention is an antimicrobial agent. Said material is selected from the group consisting of stannous fluoride, alexidine, chlorhexidine digluconate, hexetidine, copper zinc citrate and stannous pyrophosphate, triclosan, cetylpyridinium chloride and halogenated bisphenolic compounds.

Alternatively, the material of the present invention serves as a cleaning agent. Said material is selected from the group consisting of sodium alkyl sulfate, sodium lauryl sulfate, sodium coconut monoglyceride sulfonates, sodium lauryl sarcosinate, taurates, sodium lauryl sulfoacetate, sodium lauroyl isothionate, sodium laureth carboxylate, sodium dodecyl benzenesulfonate, poloxamers, polyoxyethylene sorbitan esters, fatty alcohol ethoxylates, polyethylene oxide, cocamidoppropyl betaine, sodium bicarbonate, monosodiumphosphate, sodium hydroxide, potassium hydroxide, sodium carbonate and imidazole.

Alternatively, the material of the present invention serves as an effervescing agent. Said material uses a sodium bicarbonate/citric acid system.

Alternatively, the material of the present invention serves as a tooth desensitizing agent. Said material is selected from the group consisting of fluorides, potassium citrate, potassium chloride, potassium tartrate, potassium bicarbonate, potassium oxalate and potassium nitrate.

Alternatively, the material of the present invention serves as a tooth whitening or bleaching agent. Said material is selected from the group consisting of hydrogen peroxide, carbamide peroxide metal chlorites, perborates, percarbonates, peroxyacids, persulfates, urea peroxide, calcium peroxide, calcium chlorite, barium chlorite, magnesium chlorite, lithium chlorite, sodium chlorite, potassium chlorite, hypochlorite, chlorine dioxide, sodium percarbonate, oxones, and protease.

BRIEF DESCRIPTION OF THE FIGURES

In the drawings:

FIG. 3(a) illustrates a side elevation view of a bucal portion of two lower posterior teeth similar to that shown in FIG. 1(a) and FIG. 2(e), showing periodontal disease resulting in gingival and bone recession, and showing a rolled retention device being inserted with tweezers into a furcation of a molar tooth.

FIG. 3(b) illustrates the rolled retention device in situ, positioned in the furcation.

FIG. 4(a) illustrates the retention device a configuration comprising notches (or, recesses) to facilitate interproximal placement around the interdental gingival papilla, and extensions (or, protrusions) in order to fill the col area and to overlap the gingival papilla on the exterior portions.

FIG. 4(b) illustrates the retention device similar to that shown in FIG. 4(a), in an elongated form to fill an asymmetrical col area.

FIG. 4(c) illustrates the retention device shown in FIG. 4(a) with side flaps (or, wing members) which also facilitate retention at an interproximal site and increases the area of contact of the device to a larger area around the contact area.

FIG. 4(d) illustrates the retention device in a star shaped configuration, similar in essence to that of FIGS. 4(c) and 4(d).

FIG. 4(e) illustrates the retention device in a C-shaped configuration, showing the axes about which the device may be folded to form a symmetrical (Y-Y) shaped device or asymmetrical (Z-Z) shaped device.

FIG. 6(a) illustrates a frontal (facial) device view of a strip with two distal retention devices as shown in FIG. 4(c) in order to retain the said strip between the first bicuspids (premolars) and canines by means of the retention devices which are attached to the strip by means of an extension arm.

FIG. 6(b) illustrates a top view of the embodiment of FIG. 6(a) taken along line YY-YY thereof.

FIG. 6(c) illustrates a top view of a longer strip that covers the facial side of an entire dental arch with four retention systems.

DETAILED DESCRIPTION OF THE PREFERRED EMBODIMENTS

Figure 1A:
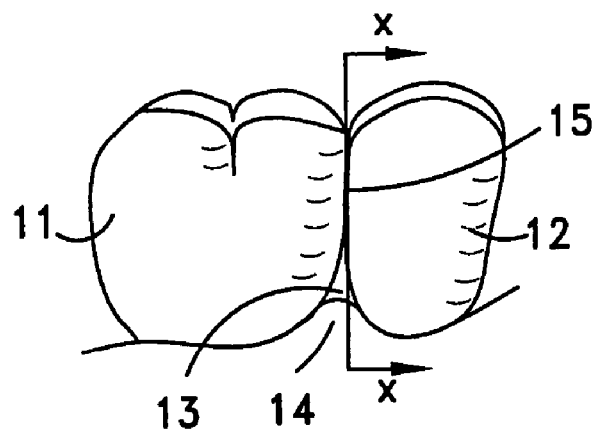
FIG. 1(a) illustrates a side, elevation view of a lingual portion of two lower posterior teeth (a molar and bicuspid (premolar)), showing the space between these two teeth (the interproximal or aproximal space), the gingival papilla and the contact area.

The present invention is defined by the claims, the contents of which are to be read as included within the disclosure of the specification, and will now be described by way of example with reference to the accompanying Figures.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The present invention relates to a device for the controlled or sustained delivery of a material or materials having a predetermined intra-oral activity to dental surfaces of the oral cavity, typically tooth surfaces or carious lesions, and in particular to interproximal sites or furcations, the device comprising a matrix or matrices containing said material or materials. The matrix or matrices is adapted for the controlled or sustained release of the active material or materials, and is further adapted for physically affixing at the dental site, for at least a predetermined time period that is correlated to the delivery of a predetermined portion of said material or materials to said site. This time period typically depends on the nature of the active material or materials and on the subject being treated, and may comprise a few seconds while a chemical activator, an electrical current, or a heat or light source such as a laser is administered to about four to eight hours during interproximal caries prevention or treatment. It is to be appreciated that a major factor in establishing the rate of release of the active material or materials is the structure of the polymeric matrix or matrices as a single uniform unit, multi-layer or a multi-location form. Thus, desired rates of release may be achieved by employing specific polymers, which are preferably cross-linked to a degree affording the desired rate of release. Matrices that are highly cross-linked would release the active material or materials more slowly, and vice versa. The man of skill in the art of pharmacy and delivery system is familiar with such considerations, which are described in many articles and textbooks, e.g., Remington's Pharmaceutical Sciences, Gennaro A. R. ed., Mack Publishing Company, Easton, Pa., 1990, which is fully incorporated herein by reference.

The release of an active agent or agents can be varied within a single matrix or by utilizing a combination of more than one matrix. There are many examples of means for varying release patterns from a single matrix. Examples include different types and degrees of cross-linkage and different additives (such as antimicrobial agents, preservatives, sterilizing agents and enzyme inhibitors) which influence the biodegradation. Furthermore, the release of even a single agent can vary by the manner it is bound in a matrix. For example, sodium fluoride can be released from a single matrix in a biphasic manner where the initial release is of loosely bound sodium fluoride and the next release is of more firmly bound sodium fluoride. Different patterns can also be obtained by using different types of fluoride, for example sodium fluoride, acidulated phosphate fluoride and an amino fluoride, which differ chemically and in molecular size. Another facet is that the matrix can create a microenvironment which excludes some salivary products such as proteins that inhibit mineralization, and others which include mineralization such as calcium phosphate and arginine. The biphasic pattern of sodium fluoride release allows an initial burst of fluoride ions to exchange with hydroxyapatite $OH^-$ groups and accelerate remineralization, then the decrease of fluoride release allows the crystals to grow by providing some fluoride, calcium and phosphate from the matrix. The latter two elements can either be added as agents to the matrix or absorbed by the matrix from the saliva. The final release also favors the deposition of calcium fluoride globules which are long term pH sensitive fluoride reservoirs.

Another approach of varying release patterns is the use of more than one matrix either as separate layers or multilocated systems. Besides causing different release patterns, the use of more than one matrix can keep different agents apart to in situ placement. Each matrix could be loaded with the same or different agent/s that could be released at different rates and/or stages by utilizing intrinsically different matrices at the chemical level or/and physical parameters. For example, the outer layer of a bilayer sphere would first be exposed to the saliva and release, for example, an effervescent cleaning system which loosens and dislodges interproximal plaque and debris and then the inner layer releases, for example, fluoride ions. Another example is the initial release of hypochlorite, which removes organic content of dentinal tubules and then a mineralizing agent or agents. (see Inaba D. et al., Caries Res. 30:218-224 (1996).) Yet another example is that the device can comprise of a coronal and an apical region where the coronal region contains an agent or agents more effective on enamel and the apical region contains an agent or agents more effective on cementum, dentin, gingival and periodontal tissue. An example of a multilayered multi-phase release system is one designed to mimic chiton radula formation which could be used to favorably alter tooth surfaces.

These matrices can comprise a single unit which was affixed one upon the other either by physical pressure or chemical bonding. They can also be formed by plating the first layer and then the same layer is plated over the dried first layer.

The present invention more particularly relates to a retention device for affixing at a dental site within the intraoral cavity, and directed at the chemical treatment of dental surfaces at the site or for chemical and/or physical restoration of the dental surfaces.

Figure 1B:
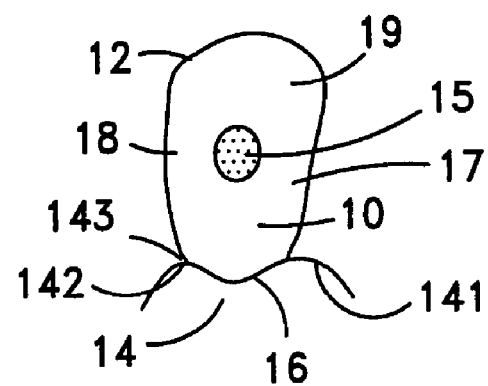
FIG. 1(b) illustrates a cross-sectional view taken along X-X of the embodiment of FIG. 1(a), showing the bicuspid (premolar) with the lingual interdental gingival papillae, the buccal (facial) interdental gingival papillae, the contact area and the gingival col.

Referring to FIG. 1(a) showing a side, elevation view of a lingual portion of a molar (11) and a bicuspid (premolar) (12), and referring to FIG. 1(b) showing a cross-sectional view taken along X-X of FIG. 1(a), an interproximal site (13) is defined herein as comprising both the area of contact (15) which is between two teeth on the medial and distal dental surfaces and the spaces surrounding area of contact (15) on the lingual (17) and buccal (facial) (18) sides of the area of contact (15), as well as at the coronal space (19) and the apical space (10). The apical space (10) is bordered apically by interdental gingival papillae (141) and (142) on the lingual (141) and buccal (facial) (142) surfaces and by a valley known as the col (16), which is the central apical base of the interproximal site (13), and which spans the interdental gingival papillae (14). The apical space (10) also includes the gingival sulcus (143) which surrounds the tooth (12) (see Glickman I Clinical Periodontology 4$^{th}$ Ed Saunders pg 18-19). The morphology and size of the above mentioned spaces are determined by the tooth size, position and shape. For instance, the contact area in the posterior teeth is located nearer the buccal surface (18) which causes a larger lingual gingival papilla (141). The contact area in anterior teeth is located nearer the lingual surface, which causes a larger lingual papilla (see Gilmore H W et al, Operative Dentistry, 3$^{rd}$ Ed., CV Mosby Company, pg. 25-26). Furthermore, the permanent anterior interdental papillary widths are less than those of the permanent molars which range from about 14 mm to 5 mm. Obviously, primary (milk) teeth also have smaller interdental papillary width dimensions. Additionally, diseases can also cause variations in shape and size. For example, periodontal disease increases the size of the spaces because of gingival and bone loss, however, on the other hand, spaces can be reduced due to gingival swelling.

It should be noted that the contact area is erroneously referred to in conventional literature as a contact point, like two marbles making contact. This is often not the case, since attrition causes the contact to flatten, and the teeth to move, which results in a contact area of about 0.3-1.0 $mm^2$ in the posterior teeth, and smaller areas in anterior and milk teeth. (see Gilmore H W, et al, op cit.)

The term, "dental surface" is defined herein as referring to any portion of a tooth or portion of the gingiva, particularly at interproximal sites and furcations.

The term, "reshape" as used herein refers to the act of reducing the overall dimensions of an object, for instance by bending, folding, rolling or otherwise collapsing the object to a desired configuration (shape), physically or chemically. To that end, the terms, "collapsing", "bending", "folding", "rolling", etc. particularly refer to the reshaping of the device of the present invention to allow the device to fit in an area of a dental site that is smaller in at least one dimension than that of the device in its original shape (e.g. prior to reshaping).

The term, "dental site" as used herein refers in general to interproximal sites and furcations. More specifically, the dental sites referred to herein comprise at least a space between adjacent dental surfaces, such that with reference to the interproximal site, the dental site includes at least a portion of the spaces (e.g. the apical space) surrounding the area of contact, and in some cases, includes the area of contact as well.

According to the present invention, in at least the reshaped configuration, the retention device is preferably shaped in an anatomical configuration according to the contours of the dental surfaces at the sites at which the device is affixed.

Figure 2A:
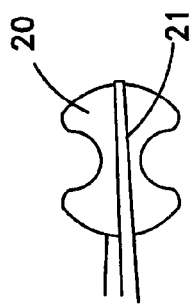
FIG. 2(a) illustrates a first embodiment of the retention device of the present invention in an H-shape.
Figure 2B:
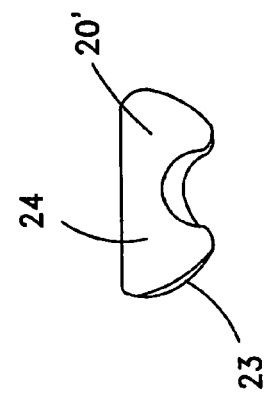
FIG. 2(b) illustrates the retention device of FIG. 2(a) gripped along the centerline of the device by the tip of tweezers.
Figure 2C:
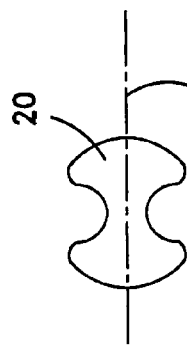
FIG. 2(c) illustrates the direction in which the retention device of FIG. 2(a) is folded while being gripped along the centerline by tweezers.
Figure 2D:
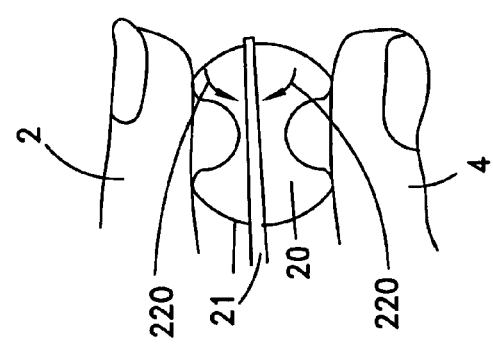
FIG. 2(d) illustrates the retention device in a folded configuration.
Figure 2F:
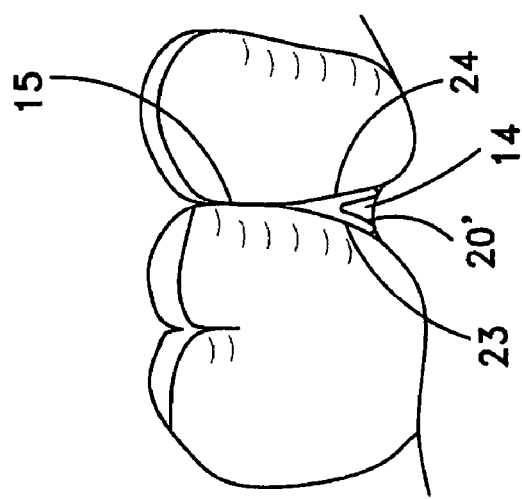
FIG. 2(f) illustrates the folded retention device positioned interproximally.
Figure 2E:
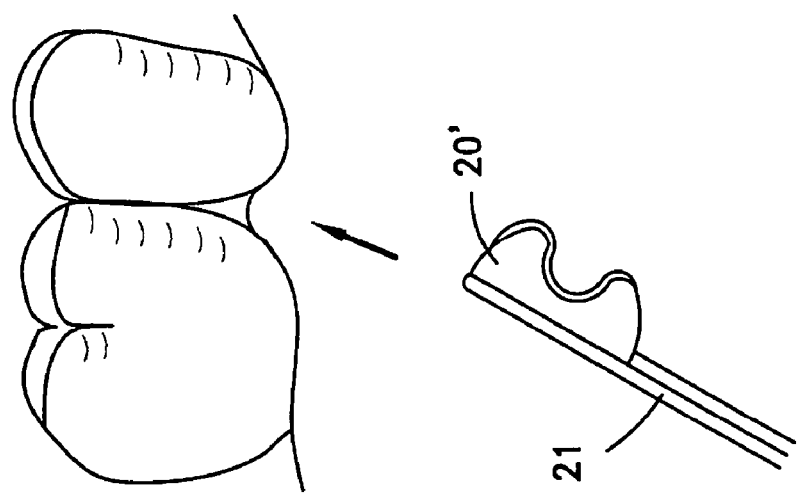
FIG. 2(e) illustrates a side elevation view of a bucal portion of two lower posterior teeth similar to that shown in FIG. 1(a), showing the folded retention device being inserted interproximally while being gripped by tweezers.

Thus, in a first aspect of the first embodiment of the present invention, and referring to FIGS. 2(a) to 2(f), the retention device (20) comprises a polymeric matrix containing an active material, and, in the first aspect, has an H-shape. Retention device (20) is folded as described herein below, for affixing at a dental site, typically below area of contact (15), and in some cases also at area of contact (15), depending on the morphology of the interproximal area, the rigidity of the device and operative procedures. Referring to FIG. 2(b), retention device (20) may be gripped along its longitudinal centerline (or, bending line) (22) (see FIG. 2(a)) by the tip of thin tweezers (21). Since retention device (20) may be stiff (and cracked if bent when dry) tweezers (21) are preferably first dampened, for instance with a water syringe from a dental unit or by dipping into a container of water prior to gripping, to allow retention device (20) to soften along the axis about which the folding is performed. As seen in FIG. 2(c), while gripping retention device (20) with tweezers, (21), the user additionally holds the outer edges of retention device (20) with fingers (2), (4), and applies enough force to fold the outer edges toward each other as indicated by arrows (220), thereby forming two flaps (23), (24), as shown in FIG. 2(d). Preferably, each outer edge is folded inwards to form an angle of approximately 30° between flaps (23), (24), however, retention device (20) may be folded more or less than 30°, and may be rolled or folded over more than once, depending, among other things, on the size of the interproximal site. Referring to FIGS. 2(e) and 2(f), folded retention device (20') is inserted interproximally in an "A" (or, upside down "V") orientation. When fixated interproximally, the apex of the "A" is situated below or at contact area (15) of adjacent teeth (11), (12), and the outer surface of flaps (23), (24) rest along the mesial and distal tooth surfaces. The inner surface of flaps (23), (24) arch over gingival (14). When absorbing the moisture and fluids in the intraoral cavity, the device softens and expands in situ, thereby causing device (20') to essentially fill all or some of the space of the interproximal site (13).

FIGS. 3(a) and 3(b) show the first aspect of the first embodiment, wherein the retention device (20") is in a rolled configuration for physically affixing in a furcation (33) using a tweezer. FIG. 3b shows rolled device HH physically fixed in the furcation (33) of the molar. When absorbing the moisture and fluids in the intraoral cavity, the device softens and expands in situ, thereby causing device (20") to essentially fill all or some of the space of the furcation (33).

A second aspect of the first embodiment is shown in FIG. 4(a), in which retention device (42) is shaped according to the contours of the apical space of the interproximal site. Retention device (42) comprises slightly convex transverse edges (43) (although straight or concave edges may be desirable in some cases), and longitudinal edges (44) comprising notches (or, recesses) (420) to accommodate the interdental gingival papilla, and extensions (or, protrusions) (422) to enhance retention at the dental surfaces, and a central extension (421) to fill the col area and also enhance retention. Alternatively, extension (422) may be excluded, elongated or shortened, and the cross-sectional shape need not be straight but can be concave on one or both surfaces. Alternative shapes for conforming to the anatomy of different dental surfaces (e.g. interproximal sites) may be desired. For example, anterior and posterior spaces differ in size and in shape from each other. Specifically, the posterior areas are wider, the position of the col is not at the midpoint, and the buccal and lingual gingival papilla are not the same size. FIG. 4(b) illustrates an alternative aspect of the second aspect, wherein notch (424) is elongated to conform to the anatomy of posterior teeth interdental gingival papillae.

Furthermore, the second aspect can comprise the apical and coronal portion differing in shape. For example, the coronal portion can be straight or dome shaped and the apical portion can be anatomically shaped, like that of FIGS. 4(a)-4(d).

FIG. 4(c) shows the second aspect of the first embodiment, wherein the retention device has wing members (430) for contacting the buccal and lingual tooth surfaces. Alternative structures may be used instead of wing members to facilitate retention at the interproximal site, and increase the contact of the retention device to a larger area around the contact area.

FIG. 4(d) shows a third aspect, wherein retention device (40) is shaped in a star-shape, which is essentially similar to the embodiment shown in FIG. 4a, but with concave edges, instead of convex edges, and which may be reshaped for affixing at a dental site; FIG. 4(b) shows a fourth aspect, showing a C-shaped retention device (41) which can be folded, for example, along Y-Y to form a symmetrically folded device, or along Z-Z to form an asymmetrically folded device. Other variations (not shown) include a star-shaped device that is elongated (i.e. stretched) in at least one plane and a disc shaped device.

Preferably according to all aspects of the first embodiment, retention device is designed to facilitate bending or folding. For example, the bending line may be indented along the entire length, or indented or punctured at intermittent points or lines (i.e. perforations) across at least a portion of the length of the bending line. Alternatively, a marking such as a line may be situated along the surface of the retention device to indicate the preferred axis about which retention device should be folded, for instance, in order to form the desired flaps. This line can be a physical form of an area which has been chemically treated to facilitate folded.

The present invention includes other aspects not shown in the figures or described herein, such as a palette shape (see U.S. Design applications No. 29/234,883 by the present inventors). Furthermore, the surfaces of the device may be flat, or one or more surfaces may be concave or convex, or any combination thereof of shapes.

Figure 5A:
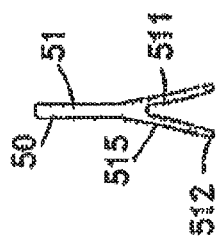
FIG. 5(a) illustrates a front view of the retention device in a Y-shape in an upside down orientation, which is anatomically contoured at the two apical portions, and slightly concaved at the portion for positioning at the contact area.
Figure 5B:
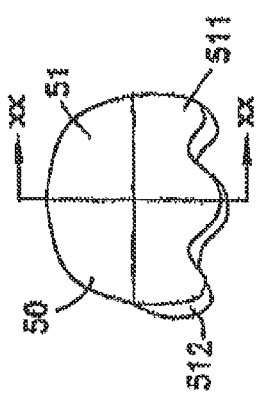
FIG. 5(b) illustrates a cross-sectional view of the embodiment of FIG. 5(a) taken along line XX-XX.

A second embodiment of the present invention, comprising all of the advantages and features of the first embodiment, mutatis mutandis, is shown in FIGS. 5(a)-5(d), with the following differences. As seen in the figures, particularly FIG. 5(b) showing a cross-sectional view taken along XX-XX of FIG. 5(a), retention device (50) is Y-shaped, for inserting and affixing in an upside down orientation at an interproximal site (FIG. 5(c)) such that the elongated portion (51) is disposed at contact area (513), and the "A" portion (515) is disposed beneath contact area (513) of adjacent teeth (52), (53), wherein flaps (511), (512) contact adjacent dental surfaces. Flaps (511) and (512) are designed to be bent slightly towards one another in order to be placed interproximally, whereafter flaps (511), (512) press slightly away from one another towards adjacent dental surfaces, thereby enhancing fixation of retention device (50) at the interproximal site. Included in this embodiment are modifications of the above description, for example, a device that only incorporates the "A" portion (515), without elongated portion (51).

Figure 5C:
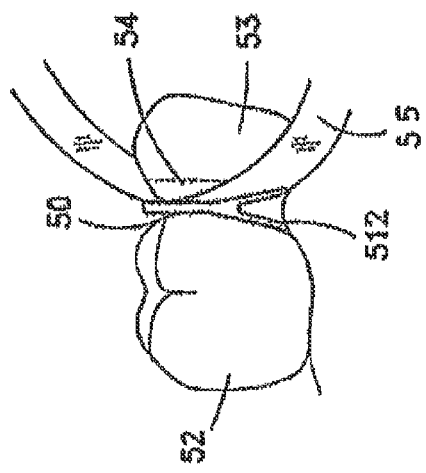
FIG. 5(c) is a side elevation view similar to FIG. 1(a) showing the device of FIG. 5(a) in situ—between the molar and bicuspid (premolar), which has a distal cavity in the bicuspid that requires a restoration.
Figure 5D:
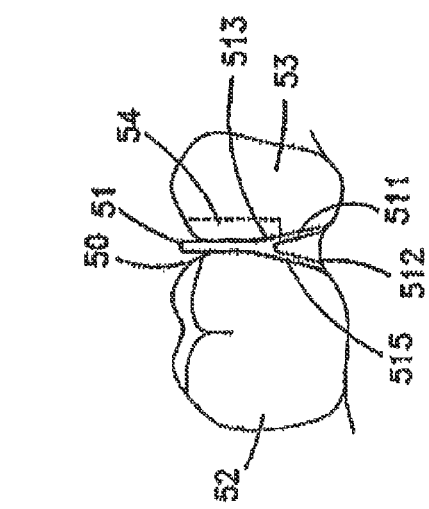
FIG. 5(d) is a side elevation view similar to FIG. 1(a) showing a matrix band being held in situ by a Y-shaped retention device between the molar and bicuspid (premolar) in order to facilitate restoration of the cavity.

According to one aspect of the second embodiment of the present invention and referring to FIGS. 5(c) and 5(d) retention device (50) can be made of a metal or plastic material for fixation at an interproximal site, in order to facilitate the restoration of a cavity (54) with an appropriate restoration material such as a tooth colored resin, glass ionomer or amalgam, independently, as shown in FIG. 5(c) or with a matrix band (55) as shown in FIG. 5(d). When flaps (511) and (512) push towards adjacent dental surfaces as described above, retention of matrix band (55) is facilitated.

A third embodiment of the present invention, comprising all of the advantages and features of the first and second embodiments, mutatis mutandis, is shown in FIGS. 6(a)-6(c), with the following differences. The third embodiment comprises a system of folded retention devices (62) attached directly or via at least one short or long extension arm (64) to an elongated strip (61) having the form of at least a portion of an entire dental arch, to allow a plurality of devices to be essentially simultaneously inserted to a dental site. FIG. 6(b) shows a cross-sectional view taken across line YY-YY of FIG. 6(a), showing strip (61) covering the facial portion of anterior teeth (63). FIG. 6(c) shows a top view of a strip (65) corresponding to an entire dental arch (65).

These applications are not limited to devices of a biodegradable, resorbable or non-resorbable nature nor any combination thereof which are left in situ, but include devices that are activated or influenced by external means such as chemical or physical intervention. This forms a tough solid device at the site. An example of a physical application such as laser irradiation using $CO_2$ lasers, Nd:YAG lasers and Argon lasers.

The physical affixing of the device of the present invention is by way of a physical property of the matrix, in particular wherein the matrix comprises a hydrophilic polymer which softens and swells in situ by the hydration thereof in the oral cavity after accommodation at the dental site. The expansion can be designed to thicken (e.g. to 250%) in size substantially more than it elongates (e.g. 20%), thereby not extruding excessively out of the interproximal and tooth domain. Optionally, the retention device comprises at least one adhesive surface or part thereof such as to enable the system to adhere or be fixed at a dental site.

Again, of course this invention is not limited to the above-described embodiments, but encompasses all the variations thereof. It is also obvious to those schooled in the art that general toxicity, allergic responses and pulp responses need to be investigated prior to applying the proposed techniques clinically.

In the system according to the present invention, the oral activity provided by the active material or materials may be medical treatment such as fluoridization, remineralization or mineralization and desensitization and/or aesthetic treatment such as tooth whitening or providing breath fresheners, and/or any other desired activity.

Thus, the different components of the matrix of the invention can comprise a range of chemicals with the following functions:

The Primary Active Fluoridating Mineralization and/or Remineralization Agents

The fluoride releasing agent/s and other mineralizing and remineralizing agent/s can be embedded within the polymeric matrix or matrices of the invention, and released from there in a controlled or sustained manner with or without at least one auxiliary chemical or physical step for example electrodes, sonification or laser application to the device in situ. The matrix or matrices described in this invention may comprise at least one primary active fluoridizing mineralization and/or remineralization agent which provides fluoride and/or other ions, which primary agents can be divided into fluoridating agents and other mineralizing and/or remineralizing agents.

Fluoridation Agents

This agent may be any single or any combination of inorganic or organic fluoride-containing pharmaceutically acceptable chemicals known or to be developed. These include, but are not limited to amine fluorides, e.g. olaflur [($N^1$-octadecyl-trimethylendiamine-N,N,N tris(2-ethanol)-2,2'-(3-n-(2-hydroxytheyl)octadecylamino]propyliminol)dihydro-floride] and dectaflur (9-octadecenylamine-hydrofluoride)), alexidine dihydrofluoride, hydrofluoride, ammonium fluoride, calcium fluoride, calcium carbonate monofluorophosphate, difluorosilane, fluoroaluminosilicate glass and any mixture thereof, hydrogen fluoride, fluoropolymer B (see U.S. Pat. No. 4,837,007), mixed salt neighborite (NaMgF3), magnesium fluoride, magnesium monofluorophosphate, potassium fluoride, lithium fluoride, indium fluoride, zirconium fluoride, copper fluoride, nickel fluoride, palladium fluoride, potassium fluorozirconate, tin fluorozirconate, sodium fluorozirconate, ammonium fluorozirconate, fluorosilicate fluorozirconate, fluoroborates, fluorozirconate, fluorostannites, fluorozirconate, sodium fluoride, stannous fluoride, stannous hexafluorozirconate, sodium hexafluorosilicate, sodium, lithium or potassium monofluorophosphate strontium fluoride and ytterbium trifluoride. Preferably, the active mineralisation agent is sodium fluoride, and/or hydrogen fluoride. This invention is not limited to the above but includes approaches such as the corporation of fluoride in the form of $Ca_5(PO_4)_3F$ (see U.S. Pat. No. 4,556,561). Variations in pH and salt types of fluorides (e.g. stannous, ammonium, titanium and amino fluorides) result in different retention of fluoride as calcium fluoride. For example, good results have been obtained using fluoride at lower pH values such as ammonium fluoride (see Jenkins, G. N. The Physiology and Biochemistry of the Mouth p. 495, 1978, Blackwell Scientific Publishing) and preferably thixotropic acidulated phosphate fluoride which can contain about 1-4% sodium fluoride with or without 0.1-0.8% hydrogen fluoride and 0.5-1.5% orthophosphoric acid (see Craig, R. G. et al Dental Materials, Properties and Manipulation p 2-28, 2.sup.nd Ed 1979 CV Mosby Co.)

The period of fluoride exposure which causes significant rehardening of a demineralized enamel surface is about 4 hours (see Koulourides, T., Art and Science of Dental Caries Research pp. 355-378, 1968; Poole, D. F. G. and Silverstone, L. M., Hard tissue Growth Repair and Remineralisation, pp. 35-52, Ciba Fondation Symposium No. 11, Elsevier Scientific Publishing Company, 1973, Pearce E. I. F and Moore, A. J., J. Dent Res 64; 416-421, 1985). Obviously the period of fluoridation required is dependent on the type of material or device herein described, its fluoride type and concentration, frequency and period of delivery, other chemical or physical interventions (such as current and laser application) and the type of surface or lesion being treated. Furthermore, the effects can also be long term because of the deposition of pH controlled fluoride reservoirs of various $CaF_2$ forms.

The acute lethal dose of fluoride (F) is 33 mg F/Kg body weight and the chronic toxicity can be 0.1 mg F/Kg. Thus the determination of the fluoride concentration range is governed by the size and number of devices used or the volume of material used, the duration of applying the material or device, the rate of fluoride ion release and the weight of the patient. Thus the concentrations can range from about 7-0.2%. (See: A guide to the use of fluorides JADA 113:504-564, 1986, prepared by the National Fluoride Task force of the NFDH).

Mineralizing and/or Remineralizing Agents

Although fluoride is to date the most effective remineralization agent, this invention and practice thereof is not limited to fluoride alone but may include or be limited to any other mineralizing or remineralization agent known or to be developed or combination thereof. Examples are amorphous minerals, crystalline minerals and organic molecules.

An advantage of amorphous minerals is that they can be easy to mold into complex shapes (see Levi-Kalisman, Y. et al J. Chem. Soc. Dalton Trans 2000: 3977-3982, 2000) such as pits and fissures, demineralized enamel or dentin. These amorphous minerals can be present in stable or unstable phases. Silica (opal) is a stable type which can be formed by the polymineralization of silicic acid which can be mediated enzymatically. On the other hand amorphous calcium carbonate and amorphous calcium phosphate are unstable as they tend to transform into stable crystalline phases. Amorphous calcium phosphate, amorphous calcium phosphate fluoride, amorphous calcium carbonate phosphate, casein phosphopeptide, amorphous calcium phosphate nancomplexes, amorphous calcium carbonate phosphate fluoride, and amorphous calcium fluoride have high solubilities, fast formation rates and fast conversion rates to apatite (see U.S. Pat. No. 5,460,803). This transformation can be controlled, for example by mimicking chiton teeth where amorphous calcium phosphate is converted into dahllite. Besides these agents there are other agents such as dicalcium phosphate dehydrate which complement fluoride in remineralizing carious lesions (Wefel, J. S, and Harless, J. D. J. Dent Res 66: 1640-1643, 1987, Takagi, S. et al Caries Res 34: 281-288 (2000)).

Examples of crystalline minerals are aragonite, brushite (see U.S. Pat. Nos. 3,679,360 and 5,605,677), calcite, dahltite, ferrihydrite, fluoroapatite, hydroxyapatite (which can also be used in dissolved synthetic forms) or in a stannous hydroxyapatite fluoride (see U.S. Pat. No. 4,923,683), lepidocrocite, magnetite, octocalcium phosphate, vaterite and whitlockite. This invention also includes a system designed to alter a tooth surface thereby enhancing its resistance to caries and other pathology. For example the process of chiton radula formation can be fully or in part adapted to alter tooth surface clinically. For example iron atoms can be introduced which precipitate a hydrated iron-oxide mineral, ferrihydrite which can then be converted to magnetite or an iron oxide mineral, lepidocrocite. Another example is amorphous calcium phosphate which can be deposited and then induced to crystallize to dahllite or hydroxyapatite (see Addadi, L. and Weiner, S. Angew, Chem. Int. Ed. Engl. 31:15, 3-169, (1992). Besides hydroxyapatite, an often found mineral at remineralized or mineralize dental sites is whitlockite (Kodaka, T. et al Caries Res 26: 69-76 (1992). These amorphous or crystalline minerals can be used to restore demineralized tissue such as interproximal caries or to seal regions such as pits and fissures by chemical or physical intervention (such as laser application), to seal areas or alter the chemical surfaces thereof.

The organic material can be macromolecules such as acidic proteins, glycoproteins and sulfated polysaccharides (Addadi, L. and Weiner, S. Angew, Chem Int Ed Engl 31:153 169, (1992)) or smaller molecules such as polyaspartic and polyglutamic acid with or without a rigid substrate adsorption (Addadi, L. et al ACS Sym. Series no. 444, 1991).

Enhancing or Other Active Agents

These agents can be the matrix or part thereof or added to the matrix (e.g. silated hydroxyethylcellulose as apatite is formed because silanol chelates calcium (see Turezyn, R. et al J. Biomater Sci. Polym Ed 11:217, (2000)) polyampholytesodium fluoride and chlorhexidine (Wefel J. S. et al. Am J. Dent. 8, 217-220 (1995); Caufield, P. W. and Navia, J. M. in the Biological Basis of dental caries, Menaker, L. 406-407, Harper and Row, (1980), benzoate-like preserving agents (see Davis, B. A. et al Caries Res 35, 331-337, (2001), Isomalt® (Takatsuka, T. J. Dent Res. Sp Iss. A #2815 (2002), silanols (see Loty C et al J. Biomed. Mat. Res. 47; 367 (2000), and dicalcium phosphate dihydrate calcium carbonate (see U.S. Pat. No. 4,556,561 and Cury, J. A. et al Caries Res. 183 (2003). Calcium and phosphate are another example (ideally 1.5 m mol/L Ca and 0.9 m mol/L PO4) see Exterkate, R. A. M. et al J. Dent Res. 72 1599-1603 (1993). Examples of suitable calcium compounds are: calcium chloride, calcium bromide, calcium nitrate, calcium acetate, calcium gluconate, calcium benzoate, calcium glycerophosphate, calcium formate, calcium fumarate, calcium lactate, calcium butyrate, calcium isobutyrate, calcium maleate, calcium maleate, calcium propionate calcium vaerate. Examples of suitable inorganic phosphates are alkali salts and ammonium salts of orthophosphoric acid such as potassium sodium or ammonium orthophosphate, monopotassium phosphate, dipotassium phosphate tripotassium phosphate, monosodium phosphate, disodium phosphate and trisodium phosphate. Other active agents are (e.g. sodium lauryl sulphate (to reduce surface tension), azacycloheptane, diphosphonate, triclosan, polyvinyl methylether with maleic anhydride copolymer resins (see Zhang et al J. Clin. Dent 14: 23-28 (2003) xylitol, erythritol, vitamin E, aloe vera and rigid beta sheet proteins such as synthetic polyaspartate and polyglutamate proteins and natural agents purified from mineralized tissue such as glycoproteins phosphorylated amino acids and acidic sulfated polysaccharides (see Addadi et al ACS Symposium series 444; Addadi et al in Chemistry and Biology of Mineralized Tissues, Ed. Slavkin, H. and Price, P. Elsevier Sci. Pub. BV 153-162 (1992)), acidic macromolecules associated with hydrophobic macromolecules such as type 1 collagen, alpha and beta chiten (see Addadi, L. and Weiner, s. Angen. Chem. Int. Ed. Engl. 31: 153-169 (1992)) and other molecules and substances such as arginine, silk and elastin. They can also be inorganic agents such as zirconium and ferric pretreatments (see Clarkson B. H. et al. J. Dent. Res. 60:1912-1920 (1981) or organic solvents such as urea designed to clean the carious lesion (see Shellis, R. P. et al Eur. J. Oral Sci 110: 392-395, (2002), being part of the system described within the invention or they can be applied prior to the device application. Other agents can be commercial cocktails such as GC Tooth Mousse Recaldent™ or experimental cocktails such as synthetic enamel preparations.

Acidifying, Buffering or pH Regulating Agents

At least one agent can be included in the matrix or matrices to enhance fluoridation, mineralization or remineralization by altering the pH (3-7) (e.g. acidulated phosphate fluoride (derived from sodium fluoride acidulated with a mixture of sodium phosphate monobasic or dibasic, and phosphoric acid or from sodium fluoride, hydrogen fluoride and orthophosphoric acid), $H_3PO_4$, citric acid, sodium citrate, or sodium bicarbonate or by inducing buffering with for example calcium carbonate, arginine and polyacrylic acid fully neutralized with alkali metal ammonium or (alkylol) amine compound sodium polyacrylate (see U.S. Pat. No. 6,106,811). Furthermore, buffers may be required to enhance cross-linkage of the matrix or matrices (e.g. phosphate buffers at pH 6.8). Those knowledgeable in the art will know that more than one stage of buffering may be required prior to the production of the final product in order to facilitate required steps such as cross-linking or curing, and optimal pH of the final device which can be low 3-4 for optimal fluoridation remineralization or mineralization or neutral in order not to etch porcelain and tooth colored restorations. Agents which influence pH can also have important roles such as in the case of the remineralization of dentin which have been reported to only occur after the extraction of proteins (see Clarkson, B. H. et al Caries Res 32: 357, 1998). Thus, the matrix or matrices could contain for example lactic acid, acetic acid, phosphoric acid or EDTA in a single matrix or on an external surface layer of a bi or multilayer device. On the other hand the dentin or enamel could be first primed with such agents using a liquid gel or an etching device, whereby the active agent is an acid, for example 37% phosphoric acid. Such a device could also be used to etch tooth surfaces prior to bonding of dental material. Another type of device could contain both the etching and bonding agent which is activated and/or cured, for example by water and/or light application (I.R., U.V. visual spectrum or lasers). One side of an interproximal device could be inactive and the second side could be an active site which could be used to fill, seal or coat interproximal sites, fissures, pits, lesions, caries, restoration defects or restoration-tooth margin defects. This second side could be a single phase or double phase system.

Another novel approach is the introduction of a buffering agent such as sodium bicarbonate during remineralization which penetrate into the subsurface lesion and then function as a buffering agent during acid challenges (see Tanaka, K. and Iijima, Y. J. of Dent. 29: 421-426 (2001)).

The Matrix and Cross-Linking Agents

The role of the matrix or matrices is to carry at least one primary active fluoridation mineralizing or remineralizing agent with or without at least one enhancing agent or other active agent and to provide the required viscosity, strength, plasticity and elasticity for application as well as the required stability or degradation pattern for the delivery of the active and any auxiliary agents, in order to provide the optimal rate and time span of ion or chemical interaction with the tooth surface and to provide a mobile environment for the appropriate ions and/or other chemicals to reach the tooth surface. Those knowledgeable and skilled in the art can alter the degradation by varying the concentrations and the degree of curing or cross-linking and type of cross-linking, or combinations thereof as well as the concentration and types of enzyme inhibitors, antimicrobial agents, preservatives and sterilizing agents which can interfere with intra-oral biodegradation. Some degradation properties may not be required in a matrix or part thereof if specific chemical or physical intervention requires instantaneous delivery.

The types of possible matrices are wide. They can include agents yet unused for dental treatment and agents such as those used as denture adhesives, impression materials, temporary, provisional or permanent restorations, sutures, perio- or surgical packs and periodontal agents (see Dental Therapeutics Digest Odontos Pub Inc.: Kay L. W. Drugs in Dentistry, Bristol 1972; O'Brien, W. J. and Ryge, G. An Outline of Dental Materials, Saunders 1978; Steinberg, D et al., J. Dent. Res. 67-208 Abstract No. 767, 1988; U.S. Pat. Nos. 5,324,519, 4,938,763, 5,278,201, 5,077,049, 5,739,176 and 5,733,950). The matrix or matrices material or materials may be sub-classified into natural products and synthetic products.

Polysaccharide polymers (e.g. agar, alginates, carboxymethylcellulose, carrageenan, cellulose, gellan gum, Kelcogel®, Kelcogel®F, Kelco Biopolymers, starches and retted flax extracts), lipids, polyisoprenes (e.g. latex rubber and gutta percha), resins and gums (e.g. tragacanth and storax) and proteins (e.g. alpha or beta chitin, soluble elastin and collagen or denatured collagen in the form of gelatin) are examples of natural products. In some cases agents may need to be treated, for example, dialyzed and de-ionized to remove impurities.

Purified collagen can be untreated or treated with fixing agents to prolong its resistance to digestion (similar to catgut surgical suture production). Denatured collagen can be impregnated with chromium salts to enhance its tensile strength and retard its absorption. A preferred polymeric matrix is a gelatin matrix, although those experienced in the art know the method of dissolution of gelatin is highly technique-sensitive and the method used can cause considerable differences in the texture. Further, gelatin, like collagen, can be lysine-cross linked with glutaraldehyde (an organelle preservant which has also been used for human aortic valve implants and dental pulp treatments; Kopel, H. M. et al., J. of Dent. for Child 47: 425-430, (1980)) and Periochip®. Another possible cross-linking agent is formaldehyde, which forms intra- and intermolecular methylene bridges between various amino acids. Further examples include but are not limited to allyl methacrylate, 2,3- or 3,4-dehydroxybenzaldehyde, glycol dimethacrylate, nordihydroguaiacetic acid, rosemarinic acid, strontium, calcium, tannic acid and hexamethylenediisocyanate and chondroitin sulfate. Again, the biocompatibility of these agents must be carefully examined even though some of them have been used clinically. Physical means of treating gelatin to induce cross-linking are also possible for example by microwave-treatment (Vandelli, M. A. et al J. of Controlled Release 96, 67-84 (2004)). The gelatin may be of any source, for example bovine or non-mammalian gelatin. Bovine gelatin is preferably used when a matrix or matrices with higher rigidity is required.

It is prudent to note that a completely natural matrix of gelatin without cross-linking can also be used with an appropriate cover. Furthermore, natural cross-linkings are also feasible, for example calcium and hydroxylysin or leucine, dihydroxylysine or leucine (Traub W., and Piez, K., A. Adv. Protein Chem. 25:243-352, 1971), lysine, arginine, proteins, polysaccharides such as dextran, lipids such as sodium docusate and dehydrodihydroxylysine or leucine (Bailey, A. J. et al., Biochem. Biophys. Res. Commun. 35:663-671 (1969)), and enzymatic cross-linking, for example, by transglutaminase (Orban J. M. et al. J of Biomedical Materials Research 68A:756-762, (2004)).

Likely candidates within the boundary of possible synthetic products that may serve for the matrices of this invention are homopolymers or copolymers with a wide molecular weight range formed by condensation, additional anionic, cationic and/or catalytic polymerization systems. Examples are acrylamide based polymers and a cationic monomer (see U.S. Pat. No. 4,837,007) cyanoacrylates, polycarbonates, polyurethane, polyester urethane dimethacrylate, polycaprolactones, ethyl triglycide methacrylate, polysulphides, povidone, polyacrylic methacrylic acid, acrylic and modifications such as poly(hydroxyethyl methacrylate), poly(methylmethacrylate) modified with small amounts of ethyl butyl or other alkyl methacrylates, polyethylene glycol, sodium polyacrylate PEG 400 and PEG 3350 and other carbomers. Some of these are indeed commercial or laboratory products such as polymethylvinylether-co-maleic anhydride and polyvinylether-co-maleic anhydride and polyvinyl pyrrolidone, carboxymethylcellulose, silated hydroxyethylcellulose or hydroxypropyl methylcellulose (Bourges et al Adv. In Colloid and Interface Sci 215-228: 2002; Bourges X. et al. Biopolymers 63:232-238: 2002) aqueous methacrylic polymer formulations for sustained and controlled release of dental and other products (e.g. Eudragit® Rohm). These polymers may require activators and cross-linking (see below). However, other agents are at times required, for example retarding agents such as hydroquinone and eugenol. Other yet different examples are zinc eugenolate, petroleatum and stearyl alcohol. Other gels may be included such as Carbopol polymers. (BF Goodrich Noveon) or a $Na_2Si\ O39H\ 2\ 0$ solution mixed with phosphoric acid and hydrofluoric acid (see U.S. Pat. No. 3,679,360).

It is to be appreciated that the degree of cross-linking is of major significance to the rate of release of the active and/or auxiliary agents. The determination of the degree of cross-linking of the polymeric matrix or matrices is within the capabilities of the man of skill in the art of pharmacy. Other factors are antimicrobial agents, preservatives, sterilizing agents inhibitors (such as inhibitors of matrix metalloproteinases (see WO 98/16503) and enzyme inhibitors which slow down the biodegradation of the matrix or matrices.

The matrices of the present invention can be strengthened not only by cross-linking, but also by other methods. For Example, U.S. Pat. No. 6,565,960 describes polymer composite compositions in which the polymer fibers, e.g. collagen fibers and gelatin, are strengthened by adding particular catechol-containing compounds, particularly compounds which have two or more catechol groups, to the polymeric material and forming a polymer of the compounds that intercalate within the polymeric material, e.g., forming a polymer composite. According to this U.S. patent, it is possible that the resulting polymer forms a scaffold-like structure throughout the polymeric material without the necessity of cross-linking the individual polymeric materials, e.g., collagen or gelatin polypeptides. This scaffolding provides synthetic polymer fibers having a tensile strength, stiffness, and strain at failure that is comparable to or better than natural polymeric material fibers. As all references cited herein, also U.S. Pat. No. 6,565,960 is fully herein incorporated.

Other novel matrices which can also be used as matrix and sealing agents, for example at pit and fissures, are Sn—Sn catenation, Sn—Cl chains or lattices or Sn protein chains (see Jodaikin, A. and Goldstein, S., J. Dent. 16:140-144, (1988)), and even combinations with fluoride, calcium, phosphate and tin (see Harris, N. O. and Christen, A. G. Primary Preventive Dentistry 4.sup.th Ed Norwalk Appleton Longe 1995; Wu. H. et al, abstract from Hua Zi Kou Qiang Yi Xue Za Zhi 18: 219-221, (2000)).

Yet another novelty is a matrix or matrices which is or includes a matrix-bound fluoride ion exchange system which can be 'recharged' with fluoride from external sources such as toothpastes, oral rinses, dental materials (see U.S. Pat. No. 5,639,840) and professionally applied fluoride systems (see Zimmerman, B. F. et al J. Dent. Res. 63:689-692 (1984); Fuji 1× GP® fast by GC Inc.).

Although the matrix or matrices are defined as a delivery system, this invention does not preclude the use of the matrix or matrices itself as a template or framework to control remineralization or mineralization based on control and design principles culled from biological mineralization or fabricated synthetic analogs.

Preservatives and Sterilizing Agents

The addition of preservatives and sterilizing agents may be advantageous particularly for long-dwelling matrices, as they will inhibit the development of various microorganisms such as bacteria, fungi and yeast, and they could play a role in inhibiting the biodegradation of the matrix or matrices, thereby influencing its longevity and the release of the active agent. Examples of preservatives are benzoic acid, biguanide, polyamino propyl biguanide, cetyl pyridinium chloride, phenol, methylparaben, metal proteins (see Horman, H. in Sigel, H. Metal Ions in Biological Systems Vol 3 New York Marcel and Dekker pg 105, 1974 and Jodaikin, A. and Goldstein, S. J. Dent 16:140-144, (1988)), and sodium bicarbonate, sorbic acid, thymol and examples of sterilizing agents are iodine, potassium and alcohol.

Stabilizing Agents

The purpose is to inhibit an unwanted or premature reaction such as reactions of calcium phosphate and fluoride by chemical means or physical means such as the use of a varnishing, coating or encapsulation agent.

Antimicrobial Agents

Included agents for therapeutic functions can be antibacterial, antiviral, antifungal and other antimicrobial agents. Indeed stannous fluoride has shown antibacterial activity (see Paine, M. L. et al JADA 129, 6977, (1998)). Other examples are alexidine, chlorhexidine digluconate, hexetidine, copper zinc citrate and stannous pyrophosphate, triclosan, cetylpyridinium chloride and halogenated bisphenolec compounds.

Cleaning Agents

The invention can function as an interproximal site cleaning system as an alternative or supplement to flossing. The invention would thus need to include agents such as a surfactant or sudsing agent which foam throughout a wide pH range. Examples of cleaning agents are sodium alkyl sulfate, sodium lauryl sulfate, sodium coconut monoglyceride sulfonates, sodium lauryl sarcosinate, taurates, sodium lauryl sulfoacetate, sodium lauroyl isothionate, sodium lauryl carboxylate, sodium dodecyl benzenesulfonate, poloxamers, polyoxyethylene sorbitan esters, fatty alcohol ethoxylates, polyethylene oxide, cocamidoppropyl betaine, hydrogen peroxide, sodium bicarbonate, monosodiumphosphate, sodium hydroxide, potassium hydroxide, sodium carbonate and imidazole. Another possibility is effervescing agents of systems such as the use of a sodium bicarbonate/citric acid system. The effervescing loosens or dislodges interproximal plaque and debris at a microscopic level thereby overcoming flossing which cannot negotiate rough surfaces, especially at the microscopic level.

Tooth Desensitizing Agents

Examples are fluorides (see above), potassium citrate, potassium chloride, potassium tartrate, potassium bicarbonate, potassium oxalate and potassium nitrate.

Whitening or Bleaching Agents

Although Whitestrips® by Crest have been marketed as a tooth whitening system in the form of a strip which contains hydrogen peroxide this invention includes a system to whiten difficult areas to access such as interproximal regions. The agents that can be used include hydrogen peroxide, carbamide peroxide, metal chlorites such as calcium chlorite, barium chlorite, magnesium chlorite, lithium chlorite, sodium chlorite, potassium chlorite, hypochlorite, perborates, percarbonates, peroxy acids, persulfates, urea peroxide, calcium peroxide, chlorine dioxide, sodium percarbonate, oxones, and even enzymes such as protease (see U.S. Pat. No. 6,521,215). Stabilizing agents may also be required, for example dipicolinic acid or sodium stannate for peroxy bleaching agents.

Gingiva and Periodontal Agents:

Agents listed in any of the above categories, antimicrobial and cleaning agents can be included, especially chlorhexidine digluconate and hydrogen peroxide (the latter can be combined with baking powder). Other examples are hyaluronic acid, thymol, doxycycline, and tetracycline hydrochloride.

Anticalculus Agents

Examples are alkalimetal pyrophosphates, hypophosphite-containing polymers, organic phosphonates, and phosphocitrates. Indeed some anti-calculus agents could enhance anti-caries activity and improve fluoride availability (see Zhang, Y. P. et al J. Clin. Dent 14: 23-28, (2003)).

Hemostatic Agents

This category includes vasoconstrictors (e.g. adrenalin), absorbable agents (e.g. oxidised cellulose, fibrin, calcium alginate), thromboplastic agents (e.g. thrombin), chemical agents (e.g. aluminum chloride, tannic acid, ferric chloride, ferric sulphate zinc chloride, alum, hyaluronic acid hydrogen peroxide) or physical plugging (e.g. the device includes bone wax). The role of a hemostat would be to stop bleeding which could hamper fluoridation or chemical treatment in regions where bleeding is caused by gingival or other bleeding.

Liquid Vehicles

Liquid vehicles may be solvents used particularly when preparing the matrix or matrices or to facilitate application. Examples are water, polydimethylsiloxane, ethyl alcohol or glycerin (glycerol) alone or in any combination.

Plasticisers and Elasticisers

Plasticisers and elasticisers may be used to modify the mechanical properties of the matrix or matrices, where needed and desired. Examples are polyethylene glycol, dibutyl phthalate, glycerol, sorbitol, mineral salts, olive oil, linseed oil, light mineral oil, polymers of ethylene propylene, polyolefins, polyacrylates polymethylates, styrene-butadiene, vinyl ethylene acetate copolymers, butadiene isoprene, gum base, silicone resins and gums, silk and elastin for example, purified from a natural rubbery protein from Ligamentum nuchae.

Another example is carboxypolymethylene which can also be incorporated in the matrix or matrices in order to increase the viscosity of the device and reduce the sorption of saliva thereby also influencing the biodegradation of the device.

According to some embodiments of present invention, the matrix or matrices may be made from any suitable material as described above, such as for example gelatin, in combination with an elasticiser, such as for example soluble elastin, sorbitol or gum base, the gelatin being preferably cross-linked and bound to soluble elastin using any suitable material such as for example glutaraldehyde, nordihydroguaiaretic acid and/or tannic acid. Such matrices have adequate plastic properties and are at the same time of sufficient toughness to maintain the mechanical integrity of the system when affixed at a dental site.

Adhering Agents

Agents may be added to facilitate adhesion to dental surface. Examples are white wax, bees wax, rosin (colophonium bases), shellac, gum mastic and polybutene.

Fillers, Softeners and Binders

The matrix or matrices may also comprise fillers and/or softeners and/or binders such as beeswax, coconut oil, corn syrup, gum Arabic, gum mastic, flour, hydrogenated castor oil, kaolin (aluminum silicate), magnesium oxide, paraffin, silicon dioxide, sodium carboxymethyl-cellulose, xanthan gum, zinc oxide or other various inorganic molecules. It should be noted that certain ions may inhibit remineralization in some cases (for example $P_2O_7$, $HCO_3$, $SiO_4$, $CrO_4$, Mg and Zn) and some inorganic fillers can be coated with water repellant coupling agents such as vinyl silane. Examples of softeners are lecithin and waxes.

Coloring or Staining Agents

These include agents to enhance the appearance of the applied at least one matrix, and dyes which are released to enhance caries detection, as discussed above. Examples are fuchsin or acid red 52 in propylene glycol. These diagnostic dyes include conventional histological stains, clinical decay detection agents and agents whose detection can be enhanced with light, for example fluorescence agents by UV light or other agents activated by intense light within the visual spectrum, or agents drawn by blotting of the lesion after the device or material is removed and the tooth surface rinsed. A color change system could also be used to indicate for example stages of degradation of the device, pH of the site and/or amounts of fluoride at the site. Another application of coloring is the need for marking of the surface to be treated with a dye in the said device which enhances the effects of lasers such as Nd.Yag (Neodymium-Yttrium Aluminum-Garnet lasers, see Miller, M, and Truhe, T. JADA 124:32 (1993)).

Flavoring or Sweetening Agents and Breath Fresheners or Sensates (Warming or Cooling Agents)

A flavoring or sweetening or sensate agent may be added to the matrix or matrices, for example, menthol, sodium saccharin, sorbitol, aspartame, sodium chloride. Also breath fresheners may be added to the matrix or matrices, for example parsley seed, methyl salicylate, sunflower oils and peppermint oil.

It is understood that the invention can include a thickening agent, a sudsing agent, a dessicating agent, an anti-plaque agent, an anti-inflammatory agent, humectants, nutrients, an analgesic or anesthetic agent, antioxidants or another therapeutic or cosmetic agent or mixtures thereof for oral and systemic use/uses.

The matrix or matrices is preferably made from a material, such as for example gelatin cross-linked by glutaraldehyde, nordihydroguaiaretic acid and/or tannic acid that is resorbable and/or biodegradable in the saliva by host enzymes, bacteria or by means of the dissolution properties of the saliva or drinks. Nonetheless, the matrix or matrices may alternatively be made from a non-resorbable material which also releases the active material or materials that is being delivered to the target area. For example, the matrix or matrices may be made from rubber latex, a polymer or any one of a large variety of sugars, lipids, nucleic acids or other proteins found in rubber latex bonded to an amine fluoride which is released in the mouth because of, for example, a host enzyme.

The matrices and devices of this invention and the manufacture thereof are not limited to the above chemical components, but encompass all their variations, and include other chemicals as only examples have been presented above. Further, the biocompatibility of these agents and their interactions need to be carefully examined and tested prior to clinical application.

While some embodiments of the invention have been described by way of illustration, it will be apparent that the invention can be carried into practice with many modifications, variations and adaptations, and with the use of numerous equivalents or alternative solutions that are within the scope of persons skilled in the art, without exceeding the scope of the claims.

The invention claimed is:

1. A retention device having a length, a depth, and a thickness for installation at a dental site, the dental site comprising an insertion space at least partially enclosed by two adjacent facing dental surfaces, and defining an insertion path into the insertion space;

the retention device comprising a first device part and second device part;

said retention device configured to have an installed configuration including the first device part in a first spatial disposition with respect to the second device part, wherein in said spatial disposition said first device part is at least one of bent or folded with respect to said second device part about a bending facilitator extending along the length of the device and positioned along a respective reference axis generally parallel to the insertion path, wherein the bending facilitator is one of the group consisting of: (a) an indented bending line; (b) a perforated bending line; (c) a physical indicating mark along a bending line; and (d) a chemically treated indicating mark along a bending line; and wherein said first device part and said second device part have respective outer-facing surfaces, each said outer-facing surface facing a respective one or another of said dental surfaces when the retention device is installed in the insertion space;

the retention device being configured in said installed configuration for providing controlled delivery to said dental site of at least one material having a predetermined intraoral activity via said outer-facing surfaces when said retention device is installed in the insertion space and in contact with said dental surfaces, said retention device comprising at least one matrix containing said at least one material;

wherein at least one of said outer-facing surfaces has a respective dimension along said reference axis corresponding to said device length, said device length being greater than a respective dimension of said at least one of said outer-facing surfaces orthogonal to said reference axis;

wherein the device is configured for being manipulated from a pre-installed configuration to said installed configuration, in which in said pre-installed configuration said first device part is in a second spatial disposition with respect to said second device part, different from said first spatial disposition, and in which said first device part is correspondingly at least one of unbent or unfolded with respect to said second device part about said respective reference axis;

wherein said retention device is resilient.

2. The retention device according to claim 1, wherein said reference axis is generally co-extensive with said adjacent facing dental surfaces of the dental site.

3. The retention device according to claim 1, wherein said dental surfaces are comprised on adjacent teeth.

4. The retention device according to claim 1, wherein in said installed configuration, said first device part is generally inclined to said second device part about said reference axis at an acute angle.

5. The retention device according to claim 1, wherein in said installed configuration, said outer-facing surfaces are facing directions generally away from one another.

6. The retention device according to claim 1, wherein in said pre-installed configuration said first device part is in a generally co-planar spatial disposition with respect to said second device part.

7. The retention device according to claim 1, wherein said retention device is made from a resilient material capable of enabling fixing of the retention device at the dental site.

8. The retention device according to claim 1, wherein the at least one matrix comprises a hydrophilic polymer to enable said retention device to be affixed by swelling in situ by the hydration of said at least one matrix in the oral cavity after accommodation of said retention device at the dental site.

9. The retention device according to claim 1, wherein said retention device is soft for easy interproximal insertion, and provides a cleaning effect which would serve as an alternative or supplement to flossing and releases said at least one material.

10. The retention device according to claim 9, wherein said at least one material is selected from the group consisting of an antimicrobial agent, a cleansing agent, a remineralizing agent, and a mineralizing agent.

11. The retention device according to claim 1, wherein said retention device is one of the group consisting of substantially biodegradable, self-degradable, substantially resorbable and substantially non-resorbable.

12. The retention device according to claim 1, wherein the at least one matrix further comprises any one of an enhancing agent for enhancing the application and release of an active material.

13. The retention device according to claim 12, wherein said at least one material is selected from the group consisting of a plasticizer, an elasticizer, a coloring agent, an adhering agent, a filler, a softener, a binder, a preserving agent, a sterilizing agent, an antimicrobial agent, an anti plaque agent, an anti inflammatory agent, an antioxidant, humectants, a nutrient analgesic agent, an anaesthetic agent, an anti calculus agent, a cleaning agent, an effervescent agent, an tooth desensitizing agent, a staining agent, a hemostatic agent, an astringent agent, a whitening agent, a bleaching agent, a flavoring agent, a sweetening agent, a breath freshener, and sensate.

14. The retention device according to claim 1, wherein the at least one material is selected from the group consisting of sodium fluoride, stannous fluoride, stannous hexafluorozirconate, calcium fluoride, difluorosilane, hydrogen fluoride, sodium monofluorophosphate, ytterbium trifluoride, sodium hexafluorosilicate, ammonium fluoride, acidulated phosphate fluoride, an amine fluoride, fluoroahuminosilicate glass, any mixture thereof, and a fluoridation agent.

15. The retention device according to claim 1, wherein the at least one material is selected from the group consisting of stannous fluoride, alexidine, chlorhexidine digluconate, hexetidine, copper zinc citrate and stannous pyrophosphate, triclosan, cetylpyridinium chloride and halogenated bisphenolic compounds, and an antimicrobial agent.

16. The retention device according to claim 1, wherein the at least one material is selected from the group consisting of a cleaning agent, a tooth desensitizing agent, a tooth whitening agent and a tooth bleaching agent.

17. A retention device according to claim 1, wherein said device is generally disc-shaped in said pre-installed configuration.

18. A retention device having a length, a depth, and a thickness for installation at a dental site, the dental site comprising an insertion space at least partially enclosed by two adjacent facing dental surfaces, and defining an insertion path into the insertion space;

the retention device configured to have a V-shaped configuration at least prior to being installed in said insertion space and, comprising at least a first device part disposed with respect to at least a second device part about a bending facilitator having a length longer than the device's depth and positioned along a reference axis to form (a) the first device part that is a first arm of said V-shaped installed configuration and (b) the second device part that is the second arm of said V-shaped installed configuration, wherein said first device part and said second device part have respective outer-facing surfaces, each said outer-facing surface configured for facing a respective one or another of said dental surfaces when the retention device is installed in said insertion space, wherein said first device part and said second device part have respective inner-facing surfaces facing one another, and wherein said device, along said bending facilitator, defines an outwardly facing free edge adjacent each said outer-facing surface;

the retention device being configured in said V-shaped configuration for providing controlled delivery to said dental site of at least one material having a predetermined intraoral activity via said outer-facing surfaces when said retention device is installed in the insertion space and in contact with said dental surfaces, said retention device comprising at least one matrix containing said at least one material;

wherein the bending facilitator is one of the group consisting of: (a) an indented bending line; (b) a perforated bending line; (c) a physical indicating mark along a bending line; and (d) a chemically treated indicating mark along a bending line;

wherein said retention device is resilient.

19. The retention device according to claim 18, wherein in said V-shaped configuration, said first device part is generally inclined to said second device part about said reference axis at an acute angle.

20. The retention device according to claim 18, wherein in a pre-installed configuration of said retention device said first device part is in a generally co-planar spatial disposition with respect to said second device part.

21. The retention device according to claim 18, wherein the at least one matrix comprises a hydrophilic polymer to enable said retention device to be affixed by swelling in situ by the hydration of said at least one matrix in the oral cavity after accommodation of said retention device at the dental site.

22. A retention device according to claim 18, wherein said device is generally disc-shaped in a non-V-shaped pre-installed configuration.

23. A retention device having a length, a depth, and a thickness for installation at a dental site, the dental site comprising an insertion space at least partially enclosed by two adjacent facing dental surfaces, and defining an insertion path into the insertion space,
the retention device comprising a reference axis generally dividing said device into a first device part and a second device part, each having a respective outer-facing surface configured for facing a respective one or another of said dental surfaces;
the retention device being configured for being installed in said insertion space with each said outer-facing surface in contact with a respective one or another of said dental surfaces, and further configured for providing controlled delivery to said dental site of at least one material having a predetermined intraoral activity via said outer-facing surfaces when said retention device is installed in the insertion space and in contact with said dental surfaces, said retention device comprising at least one matrix containing said at least one material;
the retention device further comprising a bending facilitator having a length greater than the device's depth and associated with said reference axis for facilitating bending or folding said first device part with respect to said second device part at said reference axis to provide an installed configuration in which said device, along said bending facilitator, defines an outwardly facing free edge adjacent each said outer facing surface;
wherein the bending facilitator is one of the group consisting of: (a) an indented bending line; (b) a perforated bending line; (c) a physical indicating mark along a bending line; and (d) a chemically treated indicating mark along a bending line;
wherein said retention device is resilient.

24. The retention device according to claim 23, wherein in said installed configuration, said first device part is generally inclined to said second device part about said reference axis at an acute angle.

25. The retention device according to claim 23, wherein in said installed configuration, said outer-facing surfaces are facing directions generally away from one another.

26. The retention device according to claim 23, wherein said device further comprises a relaxed, pre-installed configuration, wherein said first device part is in a generally co-planar spatial disposition with respect to said second device part.

27. The retention device according to claim 23, wherein the at least one matrix comprises a hydrophilic polymer to enable said retention device to be affixed by swelling in situ by the hydration of said at least one matrix in the oral cavity after accommodation of said retention device at the dental site.

28. A retention device according to claim 23, wherein prior to bending or folding said first device part with respect to said second device part at said reference axis, said device is generally disc-shaped.

29. A retention device for installation at a dental site, the dental site comprising an insertion space at least partially enclosed by two adjacent facing dental surfaces, and defining an insertion path into the insertion space;
the retention device comprising a first device part and a second device part, said retention device configured to have an installed configuration including said first device part in a first spatial disposition with respect to said second device part, wherein in said first spatial disposition said first device part is rolled with respect to said second device part about a respective reference axis generally parallel to the insertion path, and wherein said first device part and said second device part have respective outer-facing surfaces, each said outer-facing surface facing a respective one or another of said dental surfaces when the retention device is installed in the insertion space;
the retention device being configured in said installed configuration for providing controlled delivery to said dental site of at least one material having a predetermined intraoral activity via said outer-facing surfaces when said retention device is installed in the insertion space and in contact with said dental surfaces, said retention device comprising at least one matrix containing said at least one material;
wherein the device is configured for being manipulated from a pre-installed configuration to said installed configuration, in which in said pre-installed configuration said first device part is in a second spatial disposition with respect to said second device part, different from said first spatial disposition, and in which said first device part is unrolled with respect to said second device part about said respective reference axis;
wherein the bending facilitator is one of the group consisting of: (a) an indented bending line; (b) a perforated bending line; (c) a physical indicating mark along a bending line; and (d) a chemically treated indicating mark along a bending line;
wherein said retention device is resilient.

30. A retention device having a length, a depth, and a thickness for installation at a dental site, the dental site comprising an insertion space at least partially enclosed by two adjacent facing dental surfaces, and defining an insertion path into the insertion space;
the retention device comprising a first device part and a second device part, said retention device configured to have an installed configuration consisting of said first device part in a first spatial disposition with respect to said second device part, wherein in said spatial disposition said first device part is at least one of bent or folded with respect to said second device part about a bending facilitator having a length longer than the device's depth and wherein the device's depth is larger than the device's thickness, wherein the bending facilitator is positioned along a respective reference axis generally parallel to the insertion path, and wherein said first device part and said second device part have respective outer-facing surfaces, each said outer-facing surface facing a respective one or another of said dental surfaces when the retention device is installed in the insertion space;
the retention device being configured in said installed configuration for providing controlled delivery to said dental site of at least one material having a predetermined intraoral activity via said outer-facing surfaces when said retention device is installed in the insertion space and in contact with said dental surfaces, said retention device comprising at least one matrix containing said at least one material;
wherein the device is configured to be in said installed configuration at least prior to being installed in said insertion space;

wherein the bending facilitator is one of the group consisting of: (a) an indented bending line; (b) a perforated bending line; (c) a physical indicating mark along a bending line; and (d) a chemically treated indicating mark along a bending line;

wherein said retention device is resilient.

31. A retention device having a length, a depth, and a thickness for installation at a dental site, the dental site comprising an insertion space at least partially enclosed by two adjacent facing dental surfaces, and defining an insertion path into the insertion space;

the retention device comprising a first device part and a second device part, said retention device configured to have an installed configuration including said first device part in a first spatial disposition with respect to said second device part, wherein in said spatial disposition said first device part is folded with respect to said second device part about a bending facilitator having a length longer than the device's depth and positioned generally parallel to the insertion path, wherein said bending facilitator comprises an outwardly facing free fold edge, and wherein said first device part and said second device part have respective outer-facing surfaces, each said outer-facing surface facing a respective one or another of said dental surfaces when the retention device is installed in the insertion space;

the retention device being configured in said installed configuration for providing controlled delivery to said dental site of at least one material having a predetermined intraoral activity via said outer-facing surfaces when said retention device is installed in the insertion space and in contact with said dental surfaces, said retention device comprising at least one matrix containing said at least one material;

wherein the device is configured for being manipulated from a pre-installed configuration to said installed configuration, in which in said pre-installed configuration said first device part is in a second spatial disposition with respect to said second device part, different from said first spatial disposition, and in which said first device part is unfolded with respect to said second device part about said respective reference axis;

wherein the bending facilitator is one of the group consisting of: (a) an indented bending line; (b) a perforated bending line; (c) a physical indicating mark along a bending line; and (d) a chemically treated indicating mark along a bending line;

wherein said retention device is resilient.

32. A retention device having a length, a depth, and a thickness for installation at a dental site, the dental site comprising an insertion space at least partially enclosed by two adjacent facing dental surfaces, and defining an insertion path into the insertion space;

the retention device comprising a first device part and a second device part, said retention device configured to have an installed configuration including said first device part in a first spatial disposition with respect to said second device part, wherein in said spatial disposition said first device part is at least one of bent or folded with respect to said second device part about a bending facilitator having a length longer than the device's depth and wherein the device's depth is larger than the device's thickness, wherein the bending facilitator is positioned along a respective reference axis generally parallel to the insertion path, and wherein said first device part and said second device part have respective outer-facing surfaces, each said outer-facing surface facing a respective one or another of said dental surfaces when the retention device is installed in the insertion space;

the retention device being configured in said installed configuration for providing controlled delivery to said dental site of at least one material having a predetermined intraoral activity via said outer-facing surfaces when said retention device is installed in the insertion space and in contact with said dental surfaces, said retention device comprising at least one matrix containing said at least one material;

wherein the device is configured for being manipulated from a pre-installed configuration to said installed configuration, in which in said pre-installed configuration said first device part is in a second spatial disposition with respect to said second device part, different from said first spatial disposition, and in which said first device part is correspondingly at least one of unbent or unfolded with respect to said second device part about said respective reference axis;

wherein said device is generally disc-shaped in said pre-installed configuration;

wherein the bending facilitator is one of the group consisting of: (a) an indented bending line; (b) a perforated bending line; (c) a physical indicating mark along a bending line; and (d) a chemically treated indicating mark along a bending line;

wherein said retention device is resilient.

33. A retention device having a length, a depth, and a thickness for installation at a dental site, the dental site comprising an insertion space at least partially enclosed by two adjacent facing dental surfaces, and defining an insertion path into the insertion space;

the retention device configured to have a V-shaped configuration at least prior to being installed in said insertion space and, comprising at least a first device part disposed with respect to at least a second device part about an edge on a bending facilitator having a length longer than the device's depth and positioned along a reference axis to form (a) the first device part that is a first arm of said V-shaped installed configuration and (b) the second device part that is a second arm of said V-shaped installed configuration, wherein said first device part and said second device part have respective outer-facing surfaces, each said outer-facing surface configured for facing a respective one or another of said dental surfaces when the retention device is installed in said insertion space, wherein said first device part and said second device part have respective inner-facing surfaces facing one another, and wherein said edge comprises an outwardly facing free edge adjacent each said outer-facing surface, when the device is in the V-shaped configuration;

the retention device being configured in said V-shaped configuration for providing controlled delivery to said dental site of at least one material having a predetermined intraoral activity via said outer-facing surfaces when said retention device is installed in the insertion space and in contact with said dental surfaces, said retention device comprising at least one matrix containing said at least one material;

wherein the bending facilitator is one of the group consisting of: (a) an indented bending line; (b) a perforated bending line; (c) a physical indicating mark along a bending line; and (d) a chemically treated indicating mark along a bending line;

wherein said retention device is resilient.

* * * * *

UNITED STATES PATENT AND TRADEMARK OFFICE
CERTIFICATE OF CORRECTION

PATENT NO. : 8,287,277 B2  
APPLICATION NO. : 12/938692  
DATED : October 16, 2012  
INVENTOR(S) : Ahron Jodaikin and Hilary Jodaikin Page 1 of 1

It is certified that error appears in the above-identified patent and that said Letters Patent is hereby corrected as shown below:

Title page, item (73), Assignee:  change "Colldent V. A. Ltd." to -- Colldent Y. A. Ltd. --.

Signed and Sealed this
Eighth Day of April, 2014

Michelle K. Lee
*Deputy Director of the United States Patent and Trademark Office*